United States Patent
Ulrich, Jr. et al.

(10) Patent No.: US 8,435,302 B2
(45) Date of Patent: *May 7, 2013

(54) INSTRUMENTS AND INTERBODY SPINAL IMPLANTS ENHANCING DISC SPACE DISTRACTION

(75) Inventors: Peter F. Ulrich, Jr., Neenah, WI (US); Chad J. Patterson, Port Washington, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/480,683

(22) Filed: May 25, 2012

(65) Prior Publication Data
US 2012/0232664 A1 Sep. 13, 2012

Related U.S. Application Data

(63) Continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)
*A61B 17/88* (2006.01)

(52) U.S. Cl.
USPC ............... 623/17.16; 623/17.11; 606/100

(58) Field of Classification Search ............ 606/100; 623/17.11–17.16
See application file for complete search history.

(56) References Cited

U.S. PATENT DOCUMENTS

| 661,089 A | 11/1900 | Tanner |
|---|---|---|
| 4,904,261 A | 2/1990 | Dove et al. |

(Continued)

FOREIGN PATENT DOCUMENTS

| EP | 0599419 | 6/1994 |
|---|---|---|
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Eduardo C Robert
*Assistant Examiner* — Julianna N Harvey
(74) *Attorney, Agent, or Firm* — Stradley Ronon Stevens & Young, LLP

(57) ABSTRACT

An apparatus for distracting a disc space having an annulus. The apparatus includes a spinal implant having a pre-determined size sufficient to balance frictional fit in the disc space and elongation of the annulus. The implant has a top surface, a bottom surface, opposing lateral sides, and opposing anterior and posterior portions defining a substantially hollow center and a single vertical aperture. At least one of the opposing anterior and posterior portions presents a substantially flat impact face including an opening with an instrument retention feature. The apparatus also includes a rasp, a plurality of distractors, and an instrument able to engage and manipulate the spinal implant, the rasp, and the plurality of distractors. The size-specific rasp is adapted to clear the disc space of all soft tissue and cartilage. The plurality of distractors have progressively increasing heights adapted to distract the disc space before use of the spinal implant.

21 Claims, 20 Drawing Sheets

U.S. PATENT DOCUMENTS

| | | | |
|---|---|---|---|
| 5,015,247 A | 5/1991 | Michelson |
| 5,071,437 A | 12/1991 | Steffee |
| 5,258,098 A | 11/1993 | Wagner et al. |
| 5,306,309 A | 4/1994 | Wagner et al. |
| 5,425,772 A | 6/1995 | Brantigan |
| 5,443,514 A | 8/1995 | Steffee |
| 5,456,723 A | 10/1995 | Steinemann et al. |
| 5,507,815 A | 4/1996 | Wagner et al. |
| 5,571,188 A | 11/1996 | Ellingsen et al. |
| 5,603,338 A | 2/1997 | Beaty |
| 5,609,635 A | 3/1997 | Michelson |
| 5,702,449 A | 12/1997 | McKay |
| 5,755,798 A | 5/1998 | Papavero et al. |
| 5,766,252 A | 6/1998 | Henry et al. |
| 5,776,199 A | 7/1998 | Michelson |
| 5,860,973 A | 1/1999 | Michelson |
| 5,863,201 A | 1/1999 | Lazzara et al. |
| 5,865,845 A | 2/1999 | Thalgott |
| 5,876,453 A | 3/1999 | Beaty |
| 5,885,079 A | 3/1999 | Niznick |
| 5,888,224 A | 3/1999 | Beckers et al. |
| 5,922,029 A | 7/1999 | Wagner et al. |
| 5,968,098 A | 10/1999 | Winslow |
| 5,984,922 A | 11/1999 | McKay |
| 6,033,582 A | 3/2000 | Lee et al. |
| 6,039,762 A | 3/2000 | McKay |
| 6,059,829 A | 5/2000 | Schlaepfer et al. |
| 6,080,158 A | 6/2000 | Lin |
| 6,086,613 A | 7/2000 | Camino et al. |
| 6,096,107 A | 8/2000 | Caracostas et al. |
| 6,123,705 A | 9/2000 | Michelson |
| 6,143,032 A | 11/2000 | Schafer et al. |
| 6,176,882 B1 | 1/2001 | Biedermann et al. |
| 6,183,255 B1 | 2/2001 | Oshida |
| 6,193,757 B1 | 2/2001 | Foley et al. |
| 6,193,762 B1 | 2/2001 | Wagner et al. |
| 6,241,770 B1 | 6/2001 | Michelson |
| 6,241,771 B1 | 6/2001 | Gresser et al. |
| 6,245,108 B1 | 6/2001 | Biscup |
| 6,296,664 B1 | 10/2001 | Middleton |
| 6,302,914 B1 | 10/2001 | Michelson |
| 6,342,074 B1 | 1/2002 | Simpson |
| 6,344,057 B1 | 2/2002 | Rabbe et al. |
| 6,350,283 B1 | 2/2002 | Michelson |
| 6,375,681 B1 | 4/2002 | Truscott |
| 6,387,130 B1 | 5/2002 | Stone et al. |
| 6,395,031 B1 | 5/2002 | Foley et al. |
| 6,423,095 B1 | 7/2002 | Van Hoeck et al. |
| 6,432,140 B1 | 8/2002 | Lin |
| 6,447,544 B1 | 9/2002 | Michelson |
| 6,458,159 B1 | 10/2002 | Thalgott |
| 6,478,823 B1 | 11/2002 | Michelson |
| 6,482,233 B1 | 11/2002 | Aebi et al. |
| 6,485,517 B1 | 11/2002 | Michelson |
| 6,491,723 B1 | 12/2002 | Beaty |
| 6,558,424 B2 | 5/2003 | Thalgott |
| 6,569,201 B2 | 5/2003 | Moumene et al. |
| 6,579,318 B2 | 6/2003 | Varga et al. |
| 6,592,624 B1 | 7/2003 | Fraser et al. |
| 6,599,322 B1 | 7/2003 | Amrich et al. |
| 6,610,089 B1 | 8/2003 | Liu et al. |
| 6,620,332 B2 | 9/2003 | Amrich |
| 6,635,086 B2 | 10/2003 | Lin |
| 6,652,765 B1 | 11/2003 | Beaty |
| 6,676,703 B2 | 1/2004 | Biscup |
| 6,702,855 B1 | 3/2004 | Steinemann et al. |
| 6,719,794 B2 | 4/2004 | Gerber et al. |
| 6,726,720 B2 | 4/2004 | Ross et al. |
| 6,730,127 B2 | 5/2004 | Michelson |
| 6,740,118 B2 | 5/2004 | Eisermann et al. |
| 6,743,231 B1 | 6/2004 | Gray et al. |
| 6,758,849 B1 | 7/2004 | Michelson |
| 6,833,006 B2 | 12/2004 | Foley et al. |
| 6,890,355 B2 | 5/2005 | Michelson |
| 6,902,581 B2 | 6/2005 | Walkenhorst et al. |
| 6,911,249 B2 | 6/2005 | Wagner et al. |
| 6,923,810 B1 | 8/2005 | Michelson |
| 6,974,480 B2 | 12/2005 | Messerli et al. |
| 6,981,975 B2 | 1/2006 | Michelson |
| 7,018,418 B2 | 3/2006 | Amrich et al. |
| 7,041,137 B2 | 5/2006 | Fulton et al. |
| 7,044,972 B2 | 5/2006 | Mathys, Jr. et al. |
| 7,048,870 B1 | 5/2006 | Ellingsen et al. |
| 7,060,073 B2 | 6/2006 | Frey et al. |
| 7,066,961 B2 | 6/2006 | Michelson |
| 7,077,864 B2 | 7/2006 | Byrd, III et al. |
| 7,087,085 B2 | 8/2006 | Steinemann et al. |
| 7,112,224 B2 | 9/2006 | Liu et al. |
| 7,128,760 B2 | 10/2006 | Michelson |
| 7,137,997 B2 | 11/2006 | Paul |
| 7,144,428 B2 | 12/2006 | Anitua |
| 7,166,129 B2 | 1/2007 | Michelson |
| 7,169,183 B2 | 1/2007 | Liu et al. |
| 7,201,775 B2 | 4/2007 | Gorensek et al. |
| D541,940 S | 5/2007 | Blain |
| 7,220,280 B2 | 5/2007 | Kast et al. |
| 7,223,289 B2 | 5/2007 | Trieu et al. |
| 7,226,480 B2 | 6/2007 | Thalgott |
| 7,238,186 B2 | 7/2007 | Zdeblick et al. |
| 7,244,275 B2 | 7/2007 | Michelson |
| 7,250,060 B2 | 7/2007 | Trieu |
| 7,255,698 B2 | 8/2007 | Michelson |
| 7,288,093 B2 | 10/2007 | Michelson |
| 7,311,734 B2 | 12/2007 | Van Hoeck et al. |
| D564,095 S | 3/2008 | Blain |
| 7,347,873 B2 | 3/2008 | Paul et al. |
| D566,276 S | 4/2008 | Blain |
| 7,368,065 B2 | 5/2008 | Yang et al. |
| 7,410,501 B2 | 8/2008 | Michelson |
| 7,501,073 B2 | 3/2009 | Wen et al. |
| 7,503,933 B2 | 3/2009 | Michelson |
| 7,517,363 B2 | 4/2009 | Rogers et al. |
| D599,019 S | 8/2009 | Pimenta et al. |
| 7,569,074 B2 | 8/2009 | Eisermann et al. |
| 7,608,107 B2 | 10/2009 | Michelson |
| 7,615,078 B2 | 11/2009 | White et al. |
| 7,655,042 B2 | 2/2010 | Foley et al. |
| 7,662,186 B2 | 2/2010 | Bagga et al. |
| 7,662,190 B2 | 2/2010 | Steinemann et al. |
| 7,744,612 B2 | 6/2010 | Blain |
| 7,846,183 B2 | 12/2010 | Blain |
| 7,901,462 B2 | 3/2011 | Yang et al. |
| 7,998,172 B2 | 8/2011 | Blain |
| 8,062,304 B2 | 11/2011 | Blain et al. |
| 8,100,955 B2 | 1/2012 | Blain et al. |
| 8,142,355 B2 | 3/2012 | Blain et al. |
| 8,172,854 B2 | 5/2012 | Blain et al. |
| 8,262,737 B2 | 9/2012 | Bagga et al. |
| 2001/0014826 A1 | 8/2001 | Biedermann et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0049497 A1 | 4/2002 | Mason |
| 2002/0087212 A1* | 7/2002 | James et al. ............... 623/17.11 |
| 2002/0099443 A1 | 7/2002 | Messerli et al. |
| 2002/0128716 A1 | 9/2002 | Cohen et al. |
| 2002/0138142 A1 | 9/2002 | Castro et al. |
| 2002/0161443 A1 | 10/2002 | Michelson |
| 2002/0173854 A1 | 11/2002 | Amrich |
| 2002/0188294 A1 | 12/2002 | Couture et al. |
| 2003/0014116 A1* | 1/2003 | Ralph et al. ............... 623/17.16 |
| 2003/0083668 A1* | 5/2003 | Rogers et al. ............... 606/100 |
| 2003/0105527 A1 | 6/2003 | Bresina |
| 2003/0109928 A1 | 6/2003 | Pasquet et al. |
| 2003/0125739 A1 | 7/2003 | Bagga et al. |
| 2003/0153975 A1 | 8/2003 | Byrd, III et al. |
| 2003/0176925 A1 | 9/2003 | Paponneau |
| 2003/0181980 A1 | 9/2003 | Berry et al. |
| 2003/0181981 A1 | 9/2003 | Lemaire |
| 2003/0187506 A1 | 10/2003 | Ross et al. |
| 2003/0191531 A1 | 10/2003 | Berry et al. |
| 2004/0117020 A1 | 6/2004 | Frey et al. |
| 2004/0127993 A1 | 7/2004 | Kast et al. |
| 2004/0153154 A1 | 8/2004 | Dinkelacker |
| 2004/0153160 A1 | 8/2004 | Carrasco |
| 2004/0162616 A1* | 8/2004 | Simonton et al. ............ 623/17.11 |
| 2004/0167632 A1 | 8/2004 | Wen et al. |

| | | |
|---|---|---|
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0131416 A1* | 6/2005 | Jansen et al. ............ 606/86 |
| 2005/0147942 A1 | 7/2005 | Hall |
| 2005/0159814 A1 | 7/2005 | Karahalios |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1* | 12/2007 | Salerni et al. ............ 623/17.16 |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0195209 A1 | 8/2008 | Garcia et al. |
| 2008/0221689 A1 | 9/2008 | Chaput et al. |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2009/0005784 A1 | 1/2009 | Blain et al. |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2011/0040301 A1 | 2/2011 | Blain et al. |
| 2011/0082503 A1 | 4/2011 | Blain |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0172991 A1 | 7/2012 | Bertele et al. |

FOREIGN PATENT DOCUMENTS

| | | |
|---|---|---|
| EP | 1449544 | 8/2004 |
| EP | 2 386 274 A1 | 11/2011 |
| JP | 19968010276 | 1/1996 |
| JP | 2001170092 | 6/2001 |
| WO | 9706753 | 2/1997 |
| WO | WO 98/01091 | 1/1998 |
| WO | 0128469 | 4/2001 |
| WO | 0170144 | 9/2001 |
| WO | 0195838 | 12/2001 |
| WO | WO 2004/041131 | 5/2004 |
| WO | 2006081843 | 8/2006 |
| WO | 2006116306 | 11/2006 |
| WO | 2006119088 | 11/2006 |
| WO | WO 2006/121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011, for EP 06 75 9086.

Supplementary Partial European Search Report issued Aug. 19, 2011, for EP 06 75 9086.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

* cited by examiner

INSTRUMENTS AND INTERBODY SPINAL IMPLANTS ENHANCING DISC SPACE DISTRACTION

CROSS REFERENCE TO RELATED APPLICATIONS

This application is a continuation-in-part of U.S. patent application Ser. No. 12/151,198, filed on May 5, 2008, and pending, which is a continuation-in-part of U.S. patent application Ser. No. 11/123,359, filed on May 6, 2005, and issued as U.S. Pat. No. 7,662,186. The contents of both prior applications are incorporated by reference into this document, in their entirety and for all purposes.

TECHNICAL FIELD

The present invention relates generally to interbody spinal implants and methods of using such implants and, more particularly, to instruments and interbody spinal implants useful in enhancing disc space distraction.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This location is not the preferable seating position for an implant system, however, because only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence (defined as sinking or settling) into the softer cancellous bone of the vertebral body may arise from such improper seating.

In contrast, open ring-shaped cage implant systems are generally shaped to mimic the anatomical contour of the vertebral body. Traditional ring-shaped cages are generally comprised of allograft bone material, however, harvested from the human femur. Such allograft bone material restricts the usable size and shape of the resultant implant. For example, many of these femoral ring-shaped cages generally have a medial-lateral width of less than 25 mm. Therefore, these cages may not be of a sufficient size to contact the strong cortical bone, or apophyseal rim, of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Still further, other traditional non-allograft ring-shaped cage systems may be size-limited due to varied and complex supplemental implant instrumentation which may obstruct the disc space while requiring greater exposure of the operating space. These supplemental implant instrumentation systems also generally increase the instrument load upon the surgeon.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Traditional interbody spinal implants generally do not seat properly on the preferred structural bone located near the apophyseal rim of the vertebral body, which is primarily composed of preferred dense subchondral bone. Accordingly, there is a need in the art for interbody spinal implants which better utilize the structurally supportive bone of the apophyseal rim.

In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory. Each of these challenges is addressed in turn.

1. End-Plate Preparation

There are three traditional end-plate preparation methods. The first is aggressive end-plate removal with box-chisel types of tools to create a nice match of end-plate geometry with implant geometry. In the process of aggressive end-plate removal, however, the end-plates are typically destroyed. Such destruction means that the load-bearing implant is pressed against soft cancellous bone and the implant tends to subside.

The second traditional end-plate preparation method preserves the end-plates by just removing cartilage with curettes. The end-plates are concave; hence, if a flat implant is used, the implant is not very stable. Even if a convex implant is used, it is very difficult to match the implant geometry with the end-plate geometry, as the end-plate geometry varies from patient-to-patient and on the extent of disease.

The third traditional end-plate preparation method uses threaded fusion cages. The cages are implanted by reaming out corresponding threads in the end-plates. This method also violates the structure.

2. Implant Difficulty

Traditional anterior spinal fusion devices can also be difficult to implant. Some traditional implants with teeth have sharp edges. These edges can bind to the surrounding soft tissue during implantation, creating surgical challenges.

Typically, secondary instrumentation is used to keep the disc space distracted during implantation. The use of such instrumentation means that the exposure needs to be large enough to accommodate the instrumentation. If there is a restriction on the exposure size, then the maximum size of the implant available for use is correspondingly limited. The need for secondary instrumentation for distraction during implantation also adds an additional step or two in surgery. Still further, secondary instrumentation may sometimes over-distract the annulus, reducing the ability of the annulus to compress a relatively undersized implant. The compression provided by the annulus on the implant is important to maintain the initial stability of the implant.

For anterior spinal surgery, there are traditionally three trajectories of implants: anterior, antero-lateral, and lateral. Each approach has its advantages and drawbacks. Sometimes the choice of the approach is dictated by surgeon preference, and sometimes it is dictated by patient anatomy and biomechanics. A typical traditional implant has design features to accommodate only one or two of these approaches in a single implant, restricting intra-operative flexibility.

3. Materials of Construction

Other challenges raised by traditional devices find their source in the conventional materials of construction. Typical devices are made of PEEK or cadaver bone. Materials such as PEEK or cadaver bone do not have the structural strength to withstand impact loads required during implantation and may fracture during implantation.

PEEK is an abbreviation for polyetherether-ketone, a high-performance engineering thermoplastic with excellent chemical and fatigue resistance plus thermal stability. With a maximum continuous working temperature of 480° F., PEEK offers superior mechanical properties. Superior chemical resistance has allowed PEEK to work effectively as a metal replacement in harsh environments. PEEK grades offer chemical and water resistance similar to PPS (polyphenylene sulfide), but can operate at higher temperatures. PEEK materials are inert to all common solvents and resist a wide range of organic and inorganic liquids. Thus, for hostile environments, PEEK is a high-strength alternative to fluoropolymers.

The use of cadaver bone has several drawbacks. The shapes and sizes of the implants are restricted by the bone from which the implant is machined. Cadaver bone carries with it the risk of disease transmission and raises shelf-life and storage issues. In addition, there is a limited supply of donor bone and, even when available, cadaver bone inherently offers inconsistent properties due to its variability. Finally, as mentioned above, cadaver bone has insufficient mechanical strength for clinical application.

4. Implant Expulsion

Traditional implants can migrate and expel out of the disc space, following the path through which the implant was inserted. Typical implants are either "threaded" into place, or have "teeth" which are designed to prevent expulsion. Both options can create localized stress risers in the end-plates, increasing the chances of subsidence. The challenge of preventing implant expulsion is especially acute for PEEK implants, because the material texture of PEEK is very smooth and "slippery."

5. Implant Subsidence

Subsidence of the implant is a complex issue and has been attributed to many factors. Some of these factors include aggressive removal of the end-plate; an implant stiffness significantly greater than the vertebral bone; smaller sized implants which tend to seat in the center of the disc space, against the weakest region of the end-plates; and implants with sharp edges which can cause localized stress fractures in the end-plates at the point of contact. The most common solution to the problem of subsidence is to choose a less stiff implant material. This is why PEEK and cadaver bone have become the most common materials for spinal fusion implants. PEEK is not as hard as metals and is closer to bone hardness in some cases, but the variability can be significant with some Patient's.

6. Insufficient Room for Bone Graft

Cadaver bone implants are restricted in their size by the bone from which they are machined. Their wall thickness also has to be great to create sufficient structural integrity for their desired clinical application. These design restrictions do not leave much room for filling the bone graft material into cortical bone implants. The exposure-driven limitations on implant size narrow the room left inside the implant geometry for bone grafting even for metal implants. Such room is further reduced in the case of PEEK implants because their wall thickness needs to be greater as compared to metal implants due to structural strength needs.

7. Stress Shielding

For fusion to occur, the bone graft packed inside the implant needs to be loaded mechanically. Typically, however, the stiffness of the implant material is much greater than the adjacent vertebral bone and takes up a majority of the mechanical loads, "shielding" the bone graft material from becoming mechanically loaded. The most common solution is to choose a less stiff implant material. Again, this is why PEEK and cadaver bone have become the most common materials for spinal fusion implants. As noted above, although harder than cancellous bone, PEEK is softer than cortical bone.

8. Lack of Implant Incorporation with Vertebral Bone

In most cases, the typical fusion implant is not able to incorporate with the vertebral bone, even years after implantation. Such inability persists despite the use of a variety of different materials to construct the implants. There is a perception that cadaver bone is resorbable and will be replaced by new bone once it resorbs. Hedrocel is a composite material composed of carbon and tantalum, an inert metal, that has been used as a material for spinal fusion implants. Hedrocel is designed to allow bone in-growth into the implant. In contrast, PEEK has been reported to become surrounded by fibrous tissue which precludes it from incorporating with surrounding bone. There have also been reports of the development of new bio-active materials which can incorporate into bone. The application of such bio-active materials has been limited, however, for several reasons, including biocompatibility, structural strength, and lack of regulatory approval.

9. Limitations on Radiographic Visualization

For implants made out of metal, the metal prevents adequate radiographic visualization of the bone graft. Hence it is difficult to assess fusion, if it is to take place. PEEK is radiolucent. Traditional implants made of PEEK need to have radiographic markers embedded into the implants so that implant position can be tracked on an X-ray. Cadaver bone has some radiopacity and does not interfere with radiographic assessment as much as metal implants.

10. Cost of Manufacture and Inventory

The requirements of spinal surgery dictate that manufacturers provide implants of various foot-prints, and several heights in each foot-print. This requirement means that the manufacturer needs to carry a significant amount of inventory of implants. Because there are so many different sizes of implants, there are setup costs involved in the manufacture of each different size. The result is increased implant costs, which the manufacturers pass along to the end users by charging high prices for spinal fusion implants.

BRIEF SUMMARY OF THE INVENTION

The present invention is directed to interbody spinal implants and to methods of using such implants. The implants can be inserted, using methods of the present invention, from a variety of vantages, including anterior, antero-lateral, and lateral implantation. Certain embodiments of the present invention provide an anatomically shaped spinal implant for improved seating in the disc space, particularly in the medial-lateral aspect of the disc space, and improved utilization of the vertebral apophyseal rim. Certain embodiments of the present invention further have a highly radiused posterior portion and sides which allow for ease of implantation. Thus, the posterior portion may have a generally blunt nosed profile. Certain embodiments also allow for improved visualization of the disc space during surgical procedures while minimizing exposure of the operating space. Certain aspects of the invention reduce the need for additional instrumentation—such as chisels, reamers, or other tools—to prepare the vertebral endplate, thus minimizing the instrument load upon the surgeon.

Certain embodiments of the interbody implant are substantially hollow and have a generally oval-shaped transverse cross-sectional area. Substantially hollow, as used in this document, means at least about 33% of the interior volume of the interbody spinal implant is vacant. Further embodiments of the present invention include a body having a top surface, a bottom surface, opposing lateral sides, and opposing anterior and posterior portions. The implant includes at least one aperture that extends the entire height of the body. Thus, the aperture extends from the top surface to the bottom surface. The implant may further include at least one aperture that extends the entire transverse length of the implant body.

Still further, the substantially hollow portion may be filled with cancellous autograft bone, allograft bone, demineralized bone matrix (DBM), porous synthetic bone graft substitute, bone morphogenic protein (BMP), or combinations of those materials. The implant further includes a roughened surface topography on at least a portion of its top surface, its bottom surface, or both surfaces. The anterior portion, or trailing edge, of the implant is preferably generally greater in height than the opposing posterior portion, or leading edge. In other words, the trailing edge is taller than the leading edge. The posterior portion and lateral sides may also be generally smooth and highly radiused, thus allowing for easier implantation into the disc space. Thus, the posterior portion may have a blunt nosed profile. The anterior portion of the implant may preferably be configured to engage a delivery device, a driver, or other surgical tools. The anterior portion may also be substantially flat.

According to certain embodiments, the present invention provides an interbody spinal implant including a body having a top surface, a bottom surface, opposing lateral sides, opposing anterior and posterior portions, a substantially hollow center, and a single vertical aperture. The single vertical aperture extends from the top surface to the bottom surface, has a size and shape predetermined to maximize the surface area of the top surface and the bottom surface available proximate the anterior and posterior portions while maximizing both radiographic visualization and access to the substantially hollow center, and defines a transverse rim. The body may be non-metallic and may form one component of a composite implant; the other component is a metal plate disposed on at least one of the top and bottom surfaces of the body.

According to a specific embodiment, the present invention provides an apparatus for distracting a disc space having an annulus. The apparatus includes a spinal implant having a pre-determined size sufficient to balance frictional fit in the disc space and elongation of the annulus. The implant has a top surface, a bottom surface, opposing lateral sides, and opposing anterior and posterior portions defining a substantially hollow center and a single vertical aperture. The single vertical aperture (i) extends from the top surface to the bottom surface, (ii) has a size and shape predetermined to maximize the surface area of the top surface and the bottom surface available proximate the anterior and posterior portions while maximizing both radiographic visualization and access to the substantially hollow center, and (iii) defines a transverse rim. At least one of the opposing anterior and posterior portions presents a substantially flat impact face including an opening with an instrument retention feature. The apparatus also includes a rasp, a plurality of distractors, and an instrument able to engage and manipulate the spinal implant, the rasp, and the plurality of distractors. The size-specific rasp is adapted to clear the disc space of all soft tissue and cartilage. The plurality of distractors have progressively increasing heights adapted to distract the disc space before use of the spinal implant.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Certain embodiments of the present invention may be especially suited for placement between adjacent human vertebral bodies. The implants of the present invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over or near the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the present invention, allow for improved visualization of implant seating and fusion assessment. Interbody spinal implants, as now taught, may also facilitate osteointegration with the surrounding living bone by being biologically active.

Anterior interbody spinal implants in accordance with certain aspects of the present invention can be preferably made of a durable material such as stainless steel, stainless steel alloy, titanium, or titanium alloy, but can also be made of other durable materials such as, but not limited to, polymeric, ceramic, and composite materials. For example, certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the present invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor during implantation.

Figure 1:
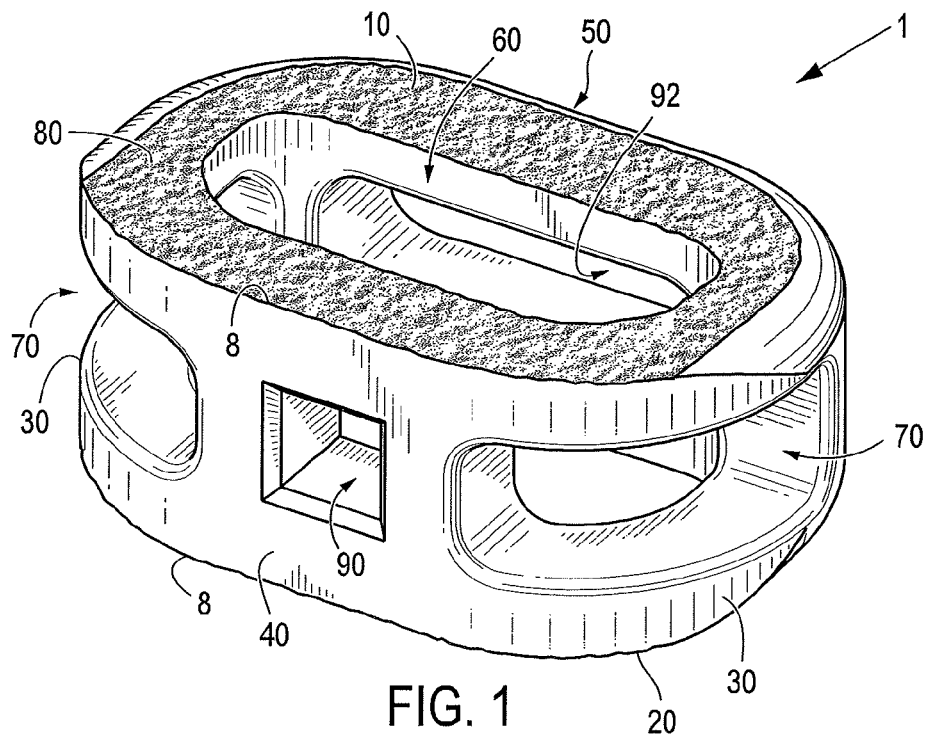
FIG. 1 shows a perspective view of a first embodiment of the interbody spinal implant having a generally oval shape and roughened surface topography on the top surface.

Referring now to the drawing, in which like reference numbers refer to like elements throughout the various figures that comprise the drawing, FIG. 1 shows a perspective view of a first embodiment of the interbody spinal implant 1 especially well adapted for use in an ALIF procedure. The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. Distinguish the roughened topography 80, however, from the disadvantageous teeth provided on the surfaces of some conventional devices.

Figure 2:
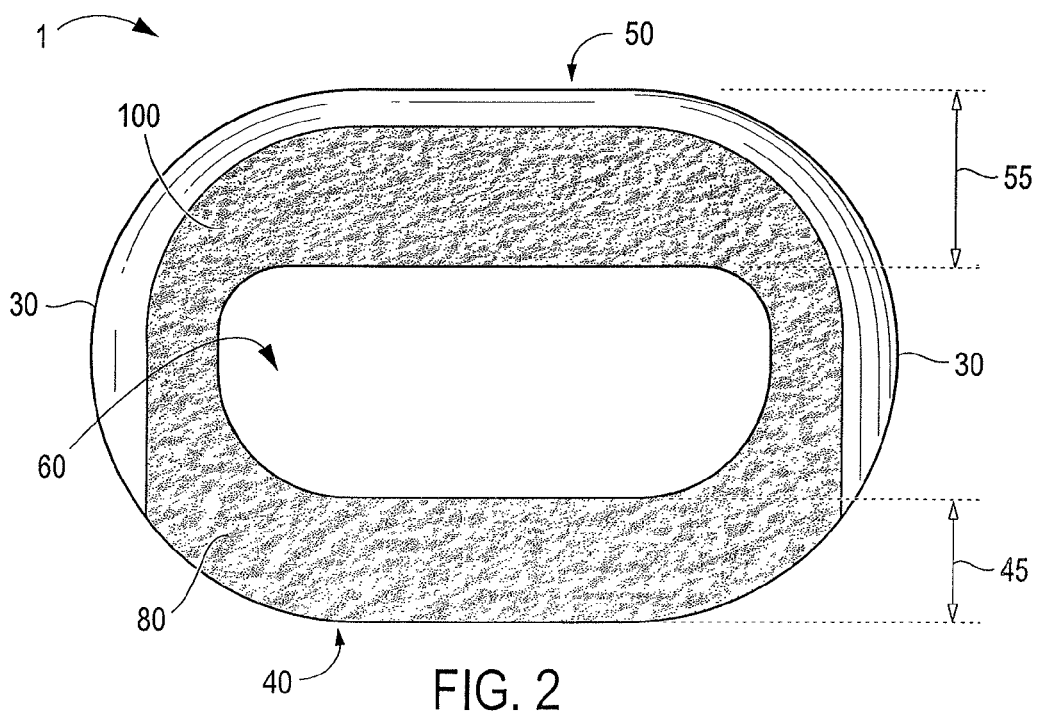
FIG. 2 depicts a top view of the first embodiment of the interbody spinal implant.

Certain embodiments of the interbody spinal implant 1 are substantially hollow and have a generally oval-shaped transverse cross-sectional area with smooth, rounded, or both smooth and rounded lateral sides and posterior-lateral corners. As used in this document, "substantially hollow" means at least about 33% of the interior volume of the interbody spinal implant 1 is vacant. The implant 1 includes at least one vertical aperture 60 that extends the entire height of the implant body. As illustrated in the top view of FIG. 2, the vertical aperture 60 further defines a transverse rim of varying width 100 having a greater posterior portion thickness 55 than an anterior portion thickness 45.

In at least one embodiment, the opposing lateral sides 30 and the anterior portion 40 have a rim thickness of about 5 mm, while the posterior portion 50 has a rim thickness of about 7 mm. Thus, the rim posterior portion thickness 55 may allow for better stress sharing between the implant 1 and the adjacent vertebral endplates and helps to compensate for the weaker posterior endplate bone. In certain embodiments, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (i.e., for the anterior portion thickness 45 to be substantially the same as the posterior portion thickness 55) or, in fact, for the posterior portion 50 to have a rim thickness less than that of the opposing lateral sides 30 and the anterior portion 40. Some studies have challenged the characterization of the posterior endplate bone as weaker.

It is generally believed that the surface of an implant determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface. Still further, it appears that these cells attach more readily to relatively rough surfaces rather than smooth surfaces. In this manner, a surface may be bioactive due to its ability to facilitate cellular attachment and osteointegration. The surface roughened topography 80 may better promote the osteointegration of certain embodiments of the present invention. The surface roughened topography 80 may also better grip the vertebral endplate surfaces and inhibit implant migration upon placement and seating.

Accordingly, the implant 1 further includes the roughened topography 80 on at least a portion of its top and bottom surfaces 10, 20 for gripping adjacent bone and inhibiting migration of the implant 1. The roughened topography 80 may be obtained through a variety of techniques including, without limitation, chemical etching, shot peening, plasma etching, laser etching, or abrasive blasting (such as sand or grit blasting). In at least one embodiment, the interbody spinal implant 1 may be comprised of titanium, or a titanium alloy, having the surface roughened topography 80. The surfaces of the implant 1 are preferably bioactive.

In a preferred embodiment of the present invention, the roughened topography 80 is obtained via the repetitive masking and chemical or electrochemical milling processes described in U.S. Pat. No. 5,258,098; No. 5,507,815; No. 5,922,029; and No. 6,193,762. Each of these patents is incorporated in this document by reference. Where the invention employs chemical etching, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.53 mm. Interbody spinal implants, in accordance with preferred embodiments of the present invention, may be comprised of titanium, or a titanium alloy, having an average surface roughness of about 100 μm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles).

Certain embodiments of the implant 1 are generally shaped to reduce the risk of subsidence, and improve stability, by maximizing contact with the apophyseal rim of the vertebral endplates. Embodiments may be provided in a variety of anatomical footprints having a medial-lateral width ranging from about 32 mm to about 44 mm. Interbody spinal implants, as now taught, generally do not require extensive supplemental or obstructive implant instrumentation to maintain the prepared disc space during implantation. Thus, the interbody spinal implant 1 and associated implantation methods, according to presently preferred aspects of the present invention, allow for larger sized implants as compared with the size-limited interbody spinal implants known in the art. This advantage allows for greater medial-lateral width and correspondingly greater contact with the apophyseal rim.

Figure 3:
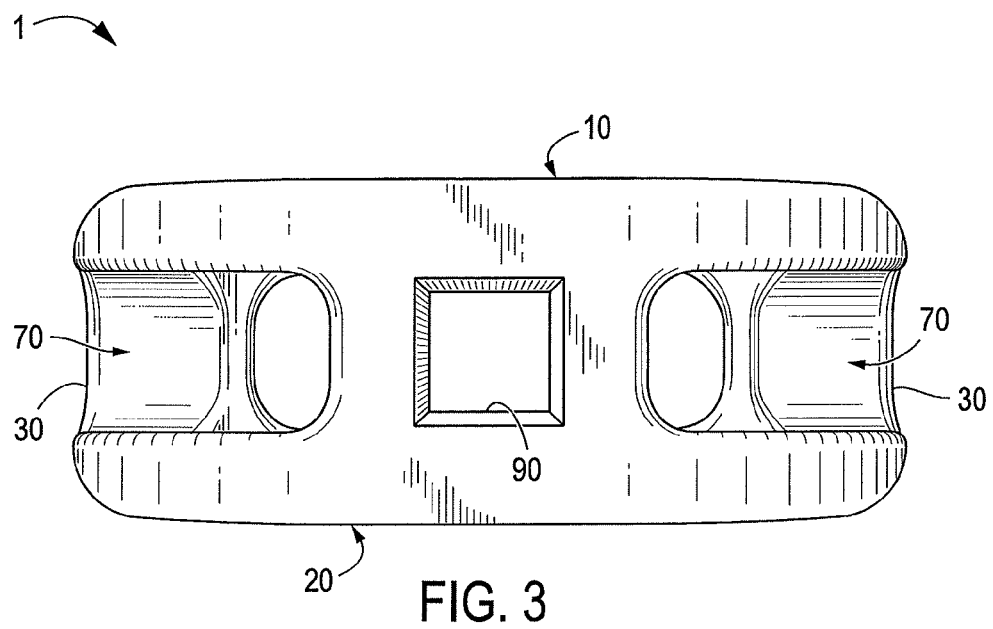
FIG. 3 depicts an anterior view of the first embodiment of the interbody spinal implant.
Figure 4:
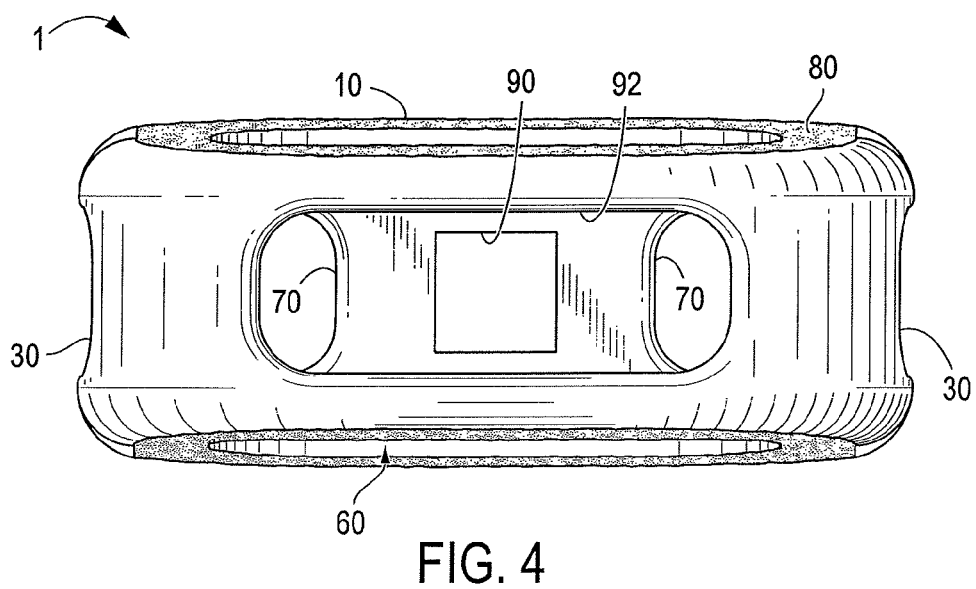
FIG. 4 depicts a posterior view of the first embodiment of the interbody spinal implant.

FIG. 3 depicts an anterior view, and FIG. 4 depicts a posterior view, of an embodiment of the interbody spinal implant 1. As illustrated in FIGS. 1 and 3, the implant 1 has an opening 90 in the anterior portion 40. As illustrated in FIGS. 3 and 4, in one embodiment the posterior portion 50 has a similarly shaped opening 90. In another embodiment, as illustrated in FIG. 1, only the anterior portion 40 has the opening 90 while the posterior portion 50 has an alternative opening 92 (which may have a size and shape different from the opening 90).

The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement.

Figure 6:
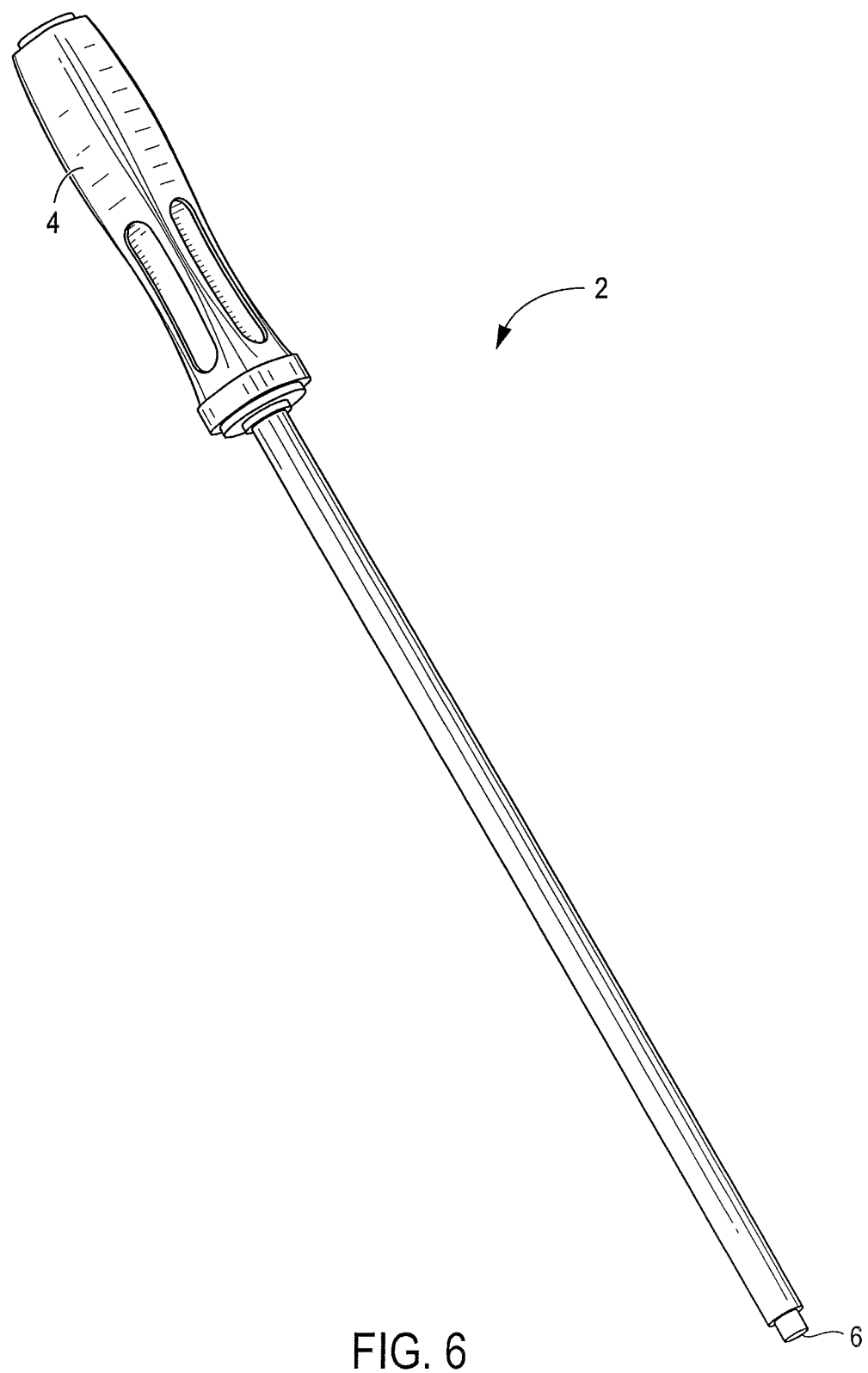
FIG. 6 shows an exemplary surgical tool (rasp and distractor holder) to be used with certain embodiments of the interbody spinal implant.

FIG. 6 shows an exemplary surgical tool, specifically an implant holder 2, to be used with certain embodiments of the interbody spinal implant 1. Typically, the implant holder 2 has a handle 4 that the caretaker can easily grasp and an end 6 that engages the opening 90. The end 6 may be threaded to engage corresponding threads in the opening 90. The size and shape of the opening 90 can be varied to accommodate a variety of tools. Thus, although the opening 90 is substantially square as illustrated in FIGS. 1, 3, and 4, other sizes and shapes are feasible.

Figure 5A:
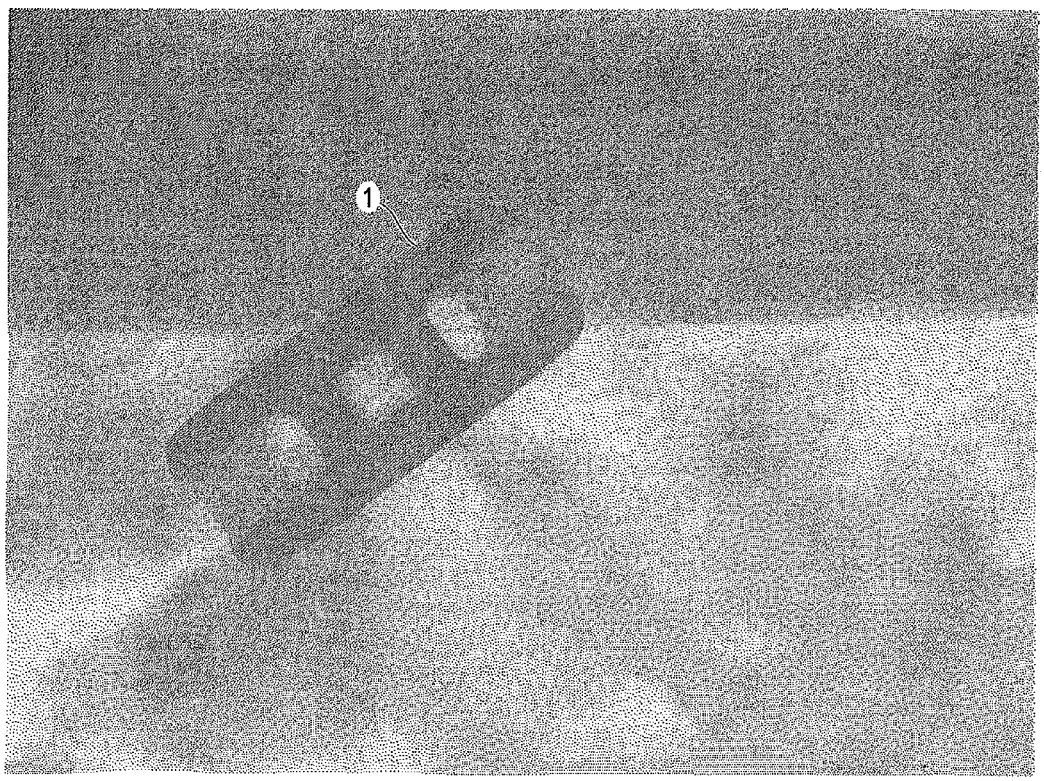
FIG. 5A depicts a first post-operative radiograph showing visualization of an embodiment of the interbody spinal implant.
Figure 5B:
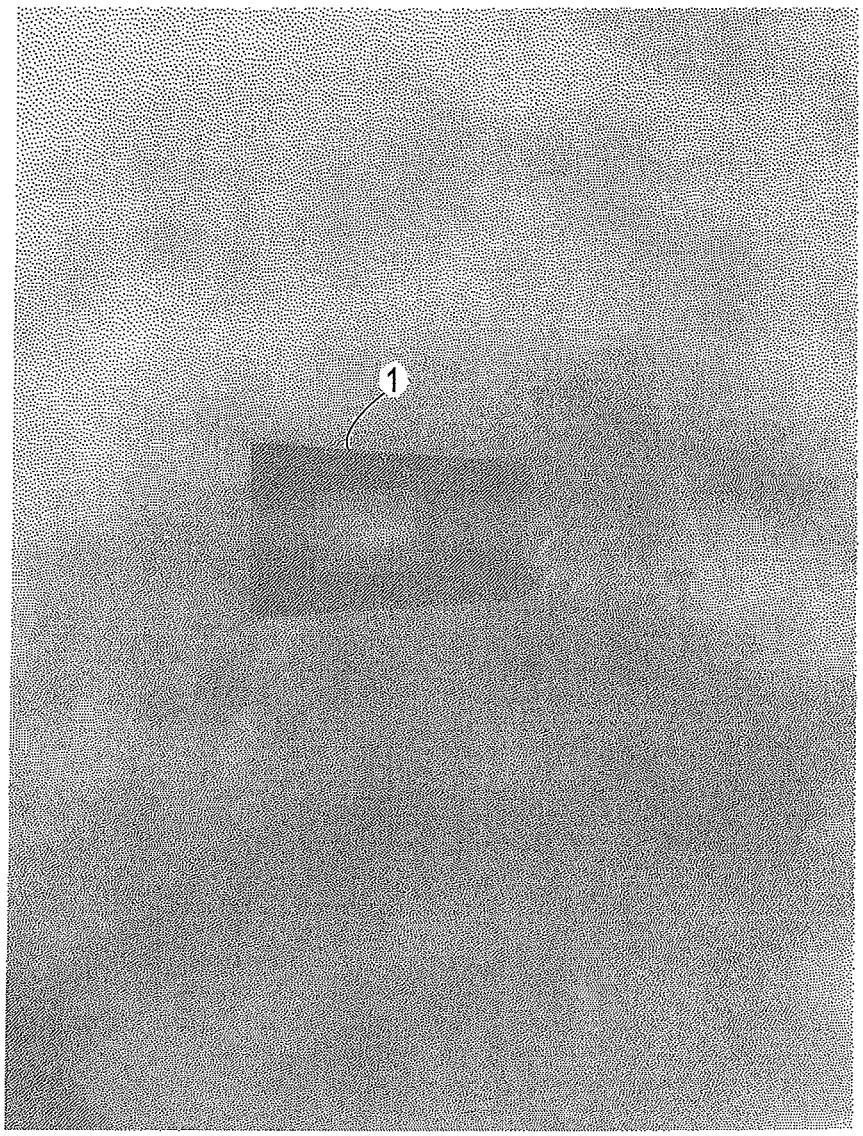
FIG. 5B depicts a second post-operative radiograph showing visualization of an embodiment of the interbody spinal implant.
Figure 5C:
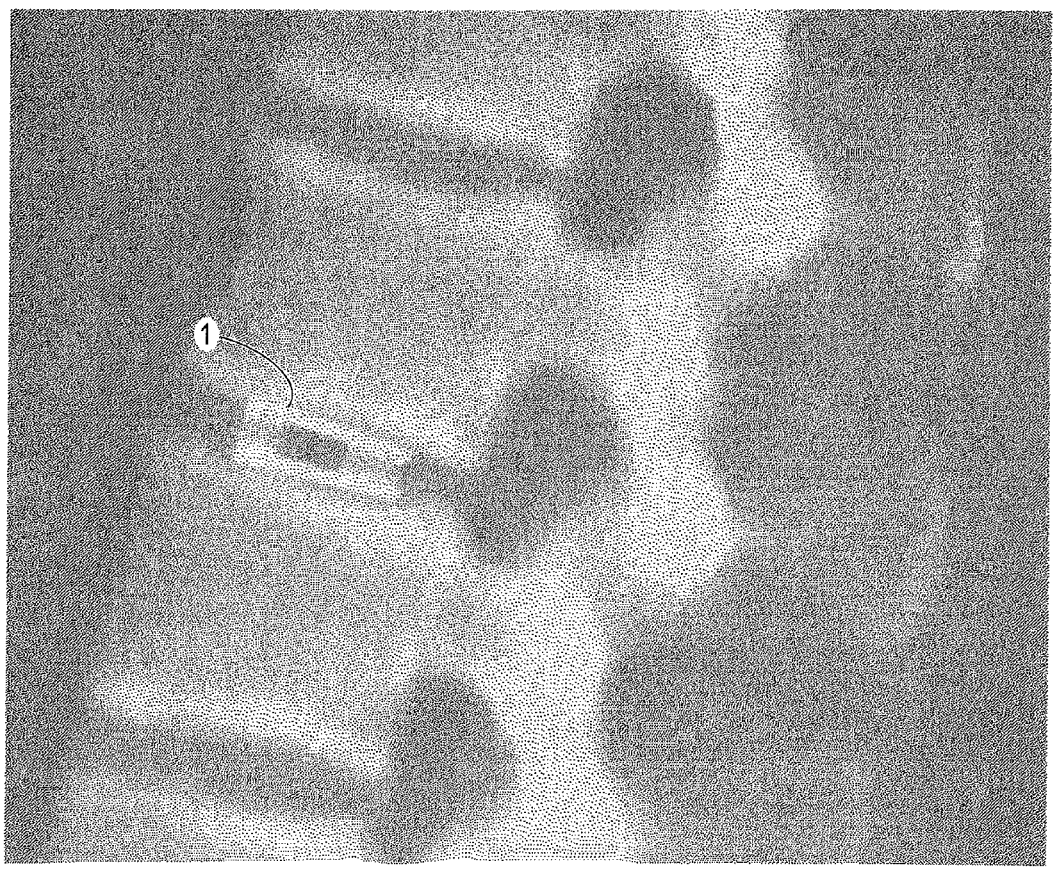
FIG. 5C depicts a third post-operative radiograph showing visualization of an embodiment of the interbody spinal implant.

The implant 1 may further include at least one transverse aperture 70 that extends the entire transverse length of the implant body. As shown in FIGS. 5A-5C, these transverse apertures 70 may provide improved visibility of the implant 1 during surgical procedures to ensure proper implant placement and seating, and may also improve post-operative assessment of implant fusion. Still further, the substantially hollow area defined by the implant 1 may be filled with cancellous autograft bone, allograft bone, DBM, porous synthetic bone graft substitute, BMP, or combinations of these materials (collectively, bone graft materials), to facilitate the formation of a solid fusion column within the spine of a patient.

The anterior portion 40, or trailing edge, of the implant 1 is preferably generally greater in height than the opposing posterior portion 50. Accordingly, the implant 1 may have a lordotic angle to facilitate sagittal alignment. The implant 1 may better compensate, therefore, for the generally less supportive bone found in the posterior regions of the vertebral endplate. The posterior portion 50 of the interbody implant 1, preferably including the posterior-lateral corners, may also be highly radiused, thus allowing for ease of implantation into the disc space. Thus, the posterior portion 50 may have a generally blunt nosed profile. The anterior portion 40 of the implant 1 may also preferably be configured to engage a delivery device, driver, or other surgical tool (and, therefore, may have an opening 90).

As illustrated in FIG. 1, the anterior portion 40 of the implant 1 is substantially flat. Thus, the anterior portion 40 provides a face that can receive impact from a tool, such as a surgical hammer, to force the implant 1 into position. The implant 1 has a sharp edge 8 where the anterior portion 40 meets the top surface 10, where the anterior portion 40 meets the bottom surface 20, or in both locations. The sharp edge or edges 8 function to resist pullout of the implant 1 once it is inserted into position.

Certain embodiments of the present invention are particularly suited for use during interbody spinal implant procedures (or vertebral body replacement procedures) and may act as a final distractor during implantation, thus minimizing the instrument load upon the surgeon. For example, in such a surgical procedure, the spine may first be exposed via an anterior approach and the center of the disc space identified. The disc space is then initially prepared for implant insertion by removing vertebral cartilage. Soft tissue and residual cartilage may then also be removed from the vertebral endplates.

Vertebral distraction may be performed using trials of various-sized embodiments of the interbody spinal implant 1. The determinatively sized interbody implant 1 may then be inserted in the prepared disc space for final placement. The distraction procedure and final insertion may also be performed under fluoroscopic guidance. The substantially hollow area within the implant body may optionally be filled, at least partially, with bone fusion-enabling materials such as, without limitation, cancellous autograft bone, allograft bone, DBM, porous synthetic bone graft substitute, BMP, or combinations of those materials. Such bone fusion-enabling material may be delivered to the interior of the interbody spinal implant 1 using a delivery device mated with the opening 90 in the anterior portion 40 of the implant 1. Interbody spinal implants 1, as now taught, are generally larger than those currently known in the art, and therefore have a correspondingly larger hollow area which may deliver larger volumes of fusion-enabling bone graft material. The bone graft material may be delivered such that it fills the full volume, or less than the full volume, of the implant interior and surrounding disc space appropriately.

Figure 9:
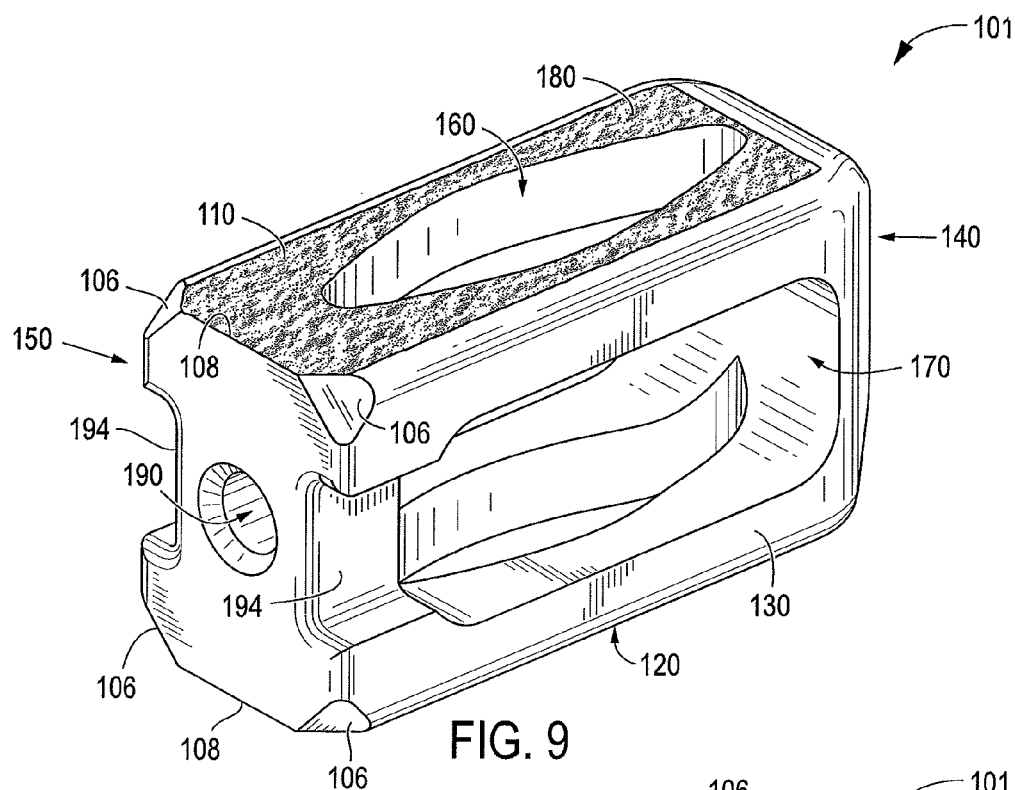
FIG. 9 shows a perspective view from the front of another embodiment of the interbody spinal implant according to the present invention.
Figure 10:
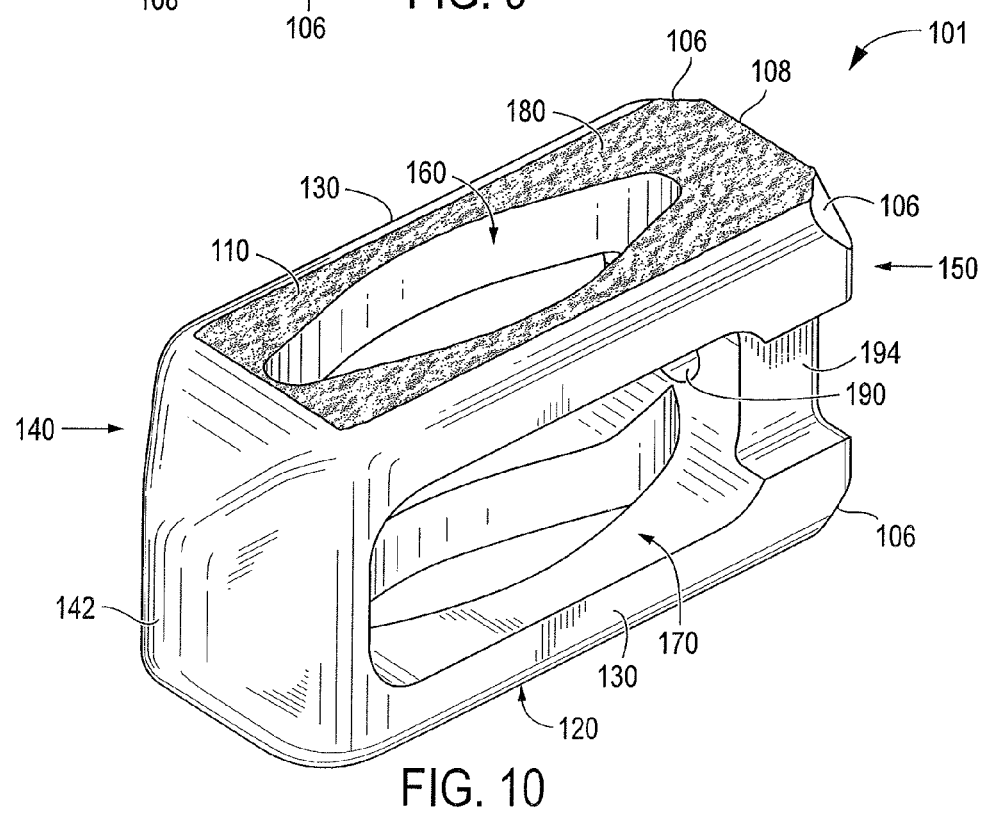
FIG. 10 shows a perspective view from the rear of the embodiment of the interbody spinal implant illustrated in FIG. 9.

As noted above, FIG. 1 shows a perspective view of one embodiment of the present invention, the interbody spinal implant 1, which is especially well adapted for use in an ALIF procedure. Other embodiments of the present invention are better suited for PLIF, TLIF, or cervical fusion procedures. Specifically, FIGS. 9 and 10 show perspective views, from the front and rear, respectively, of an embodiment of an interbody spinal implant 101 especially well adapted for use in a PLIF procedure. The interbody spinal implant 101 includes a body having a top surface 110, a bottom surface 120, opposing lateral sides 130, and opposing anterior 140 and posterior 150 portions. One or both of the top surface 110 and the bottom surface 120 has a roughened topography 180 for gripping adjacent bone and inhibiting migration of the implant 101.

Certain embodiments of the interbody spinal implant 101 are substantially hollow and have a generally rectangular shape with smooth, rounded, or both smooth and rounded lateral sides and anterior-lateral corners. As best shown in FIG. 10, the anterior portion 140 may have a tapered nose 142 to facilitate insertion of the implant 101. To further facilitate insertion, the implant 101 has chamfers 106 at the corners of its posterior portion 150. The chamfers 106 prevent the implant 101 from catching upon insertion, risking potential damage such as severed nerves, while still permitting the implant 101 to have a sharp edge 108.

As illustrated in FIG. 9, the posterior portion 150 of the implant 101 is substantially flat. Thus, the posterior portion 150 provides a face that can receive impact from a tool, such as a surgical hammer, to force the implant 101 into position. The implant 101 has a sharp edge 108 between the chamfers 106 where the posterior portion 150 meets the top surface 110, where the posterior portion 150 meets the bottom surface 120, or in both locations. The sharp edge or edges 108 function to resist pullout of the implant 101 once it is inserted into position.

The implant 101 includes at least one vertical aperture 160 that extends the entire height of the implant body. As illustrated in the top view of FIG. 11, the vertical aperture 160 further defines a transverse rim 200. The size and shape of the vertical aperture 160 are carefully chosen to achieve a preferable design trade off for the particular application envisioned for the implant 101. Specifically, the vertical aperture 160 seeks to maximize the surface area of the top surface 110 and the bottom surface 120 available proximate the anterior 140 and posterior 150 portions while maximizing both radiographic visualization and access to the bone graft material toward the center of the top 110 and bottom 120 surfaces. Thus, the size and shape of the vertical aperture 160 are predetermined by the application. By "predetermined" is meant determined beforehand, so that the predetermined size and shape are determined, i.e., chosen or at least known, before the implant 101 is selected for insertion.

Figure 11:
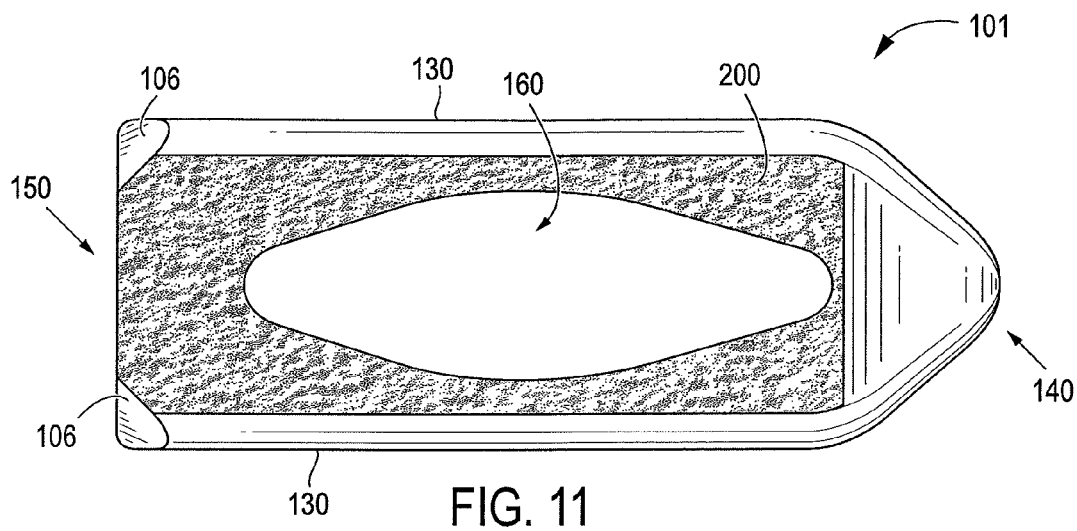
FIG. 11 is a top view of the interbody spinal implant illustrated in FIGS. 9 and 10.

In the particular example shown in FIGS. 9-11, the width of the implant 101 between the two lateral sides 130 is approximately 9 mm. The shape of the vertical aperture 160 approximates, in cross section, that of an American football. The center of the vertical aperture 160, which defines the maximum width of the vertical aperture 160, is about 5 mm. Thus, the rim thickness 200 on either side of the vertical aperture 160 adjacent the center of the vertical aperture 160 is about 2 mm. These dimensions permit ample engagement between the bone graft material contained within the implant 101 and bone.

The vertical aperture 160 tapers from its center to its ends along a longitudinal distance of about 7.75 mm (thus, the total length of the vertical aperture 160 is about 15.5 mm). This shape leaves intact much of the rim thickness 200 in the areas around the ends of the vertical aperture 160. These areas may allow for better stress sharing between the implant 101 and the adjacent vertebral endplates. Thus, the transverse rim 200 has a generally large surface area and contacts the vertebral endplate.

As illustrated in FIG. 9, the implant 101 has an opening 190 in the posterior portion 150. The opening 190 has a number of functions. One function is to facilitate manipulation of the implant 101 by the caretaker. Thus, the caretaker may insert a surgical tool (FIG. 6 shows an exemplary surgical tool, the implant holder 2) into the opening 190 and, through the engagement between the surgical tool and the opening 190, manipulate the implant 101. The opening 190 may be threaded to enhance the engagement.

The implant 101 may also have an Implant Holding Feature (IHF) 194 instead of or in addition to the opening 190. As illustrated in FIG. 9, the IHF 194 is located proximate the opening 190 in the posterior portion 150. In this particular example, the IHF 194 is a U-shaped notch. Like the opening 190, the IHF 194 has a number of functions, one of which is to facilitate manipulation of the implant 101 by the caretaker. Other functions of the opening 190 and the IHF 194 are to increase visibility of the implant 101 during surgical procedures and to enhance engagement between bone graft material and adjacent bone.

The implant 101 may further include at least one transverse aperture 170. Like the vertical aperture 160, the size and shape of the transverse aperture 170 are carefully chosen (and predetermined) to achieve a preferable design trade off for the particular application envisioned for the implant 101. Specifically, the transverse aperture 170 should have minimal dimensions to maximize the strength and structural integrity of the implant 101. On the other hand, the transverse aperture 70 should have maximum dimensions to (a) improve the visibility of the implant 101 during surgical procedures to ensure proper implant placement and seating, and to improve post-operative assessment of implant fusion, and (b) to facilitate engagement between bone graft material and adjacent bone. The substantially hollow area defined by the implant 101 may be filled with bone graft materials to facilitate the formation of a solid fusion column within the spine of a patient.

Figure 12:
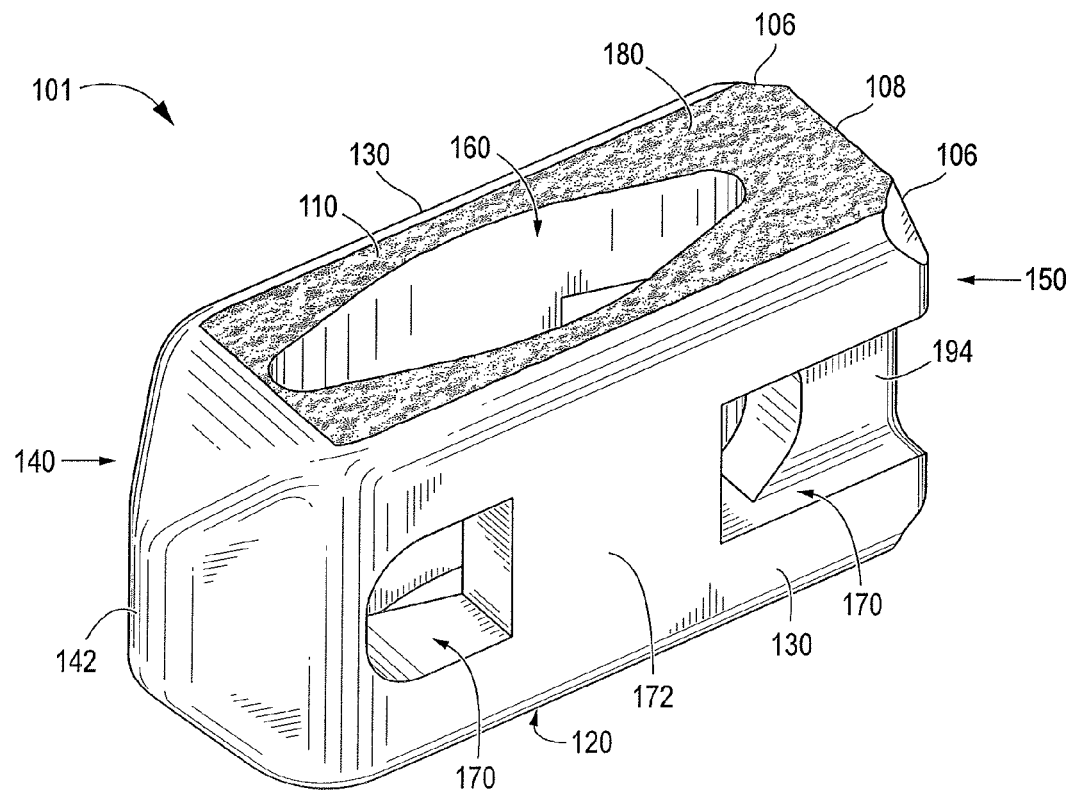
FIG. 12 shows a perspective view from the rear, like FIG. 10, of the interbody spinal implant illustrated in FIGS. 9-11 highlighting an alternative transverse aperture.

As shown in FIGS. 9 and 10, the transverse aperture 170 extends the entire transverse length of the implant body and nearly the entire height of the implant body. Thus, the size and shape of the transverse aperture 170 approach the maximum possible dimensions for the transverse aperture 170. Like FIG. 10, FIG. 12 shows a perspective view from the rear of the interbody spinal implant 101. FIG. 12 highlights, however, an alternative transverse aperture 170.

As illustrated in FIG. 12, the transverse aperture 170 is broken into two, separate sections by an intermediate wall 172. Thus, the dimensions of the transverse aperture 170 shown in FIG. 12 are much smaller than those for the transverse aperture 170 shown in FIG. 10. The section of the transverse aperture 170 proximate the IHF 194 is substantially rectangular in shape; the other section of the transverse aperture 170 has the shape of a curved arch. Other shapes and dimensions are suitable for the transverse aperture 170. In particular, all edges of the transverse aperture 170 may be rounded, smooth, or both. The intermediate wall 172 may be made of the same material as the remainder of the implant 101 (e.g., metal), or it may be made of another material (e.g., PEEK) to form a composite implant 101. The intermediate wall 172 may offer one or more of several advantages, including reinforcement of the implant 101 and improved bone graft containment.

The embodiment of the present invention illustrated in FIGS. 9-12 is especially well suited for a PLIF surgical procedure. TLIF surgery is done through the posterior (rear) part of the spine and is essentially like an extended PLIF procedure. The TLIF procedure was developed in response to some of the technical problems encountered with a PLIF procedure. The main difference between the two spine fusion procedures is that the TLIF approach to the disc space is expanded by removing one entire facet joint; a PLIF procedure is usually done on both sides by only taking a portion of each of the paired facet joints.

By removing the entire facet joint, visualization into the disc space is improved and more disc material can be removed. Such removal should also provide for less nerve retraction. Because one entire facet is removed, the TLIF procedure is only done on one side: removing the facet joints on both sides of the spine would result in too much instability. With increased visualization and room for dissection, one or both of a larger implant and more bone graft can be used in the TLIF procedure. Theoretically, these advantages can allow the spine surgeon to distract the disc space more and realign the spine better (re-establish the normal lumbar lordosis).

Although the TLIF procedure offers some improvements over a PLIF procedure, the anterior approach in most cases still provides the best visualization, most surface area for healing, and the best reduction of any of the approaches to the disc space. These advantages must be weighed, however, against the increased morbidity (e.g., unwanted aftereffects and postoperative discomfort) of a second incision. Probably the biggest determinate in how the disc space is approached is the comfort level that the spine surgeon has with an anterior approach for the spine fusion surgery. Not all spine surgeons are comfortable with operating around the great vessels (aorta and vena cava) or have access to a skilled vascular surgeon to help them with the approach. Therefore, choosing one of the posterior approaches for the spine fusion surgery is often a more practical solution.

Figure 13:
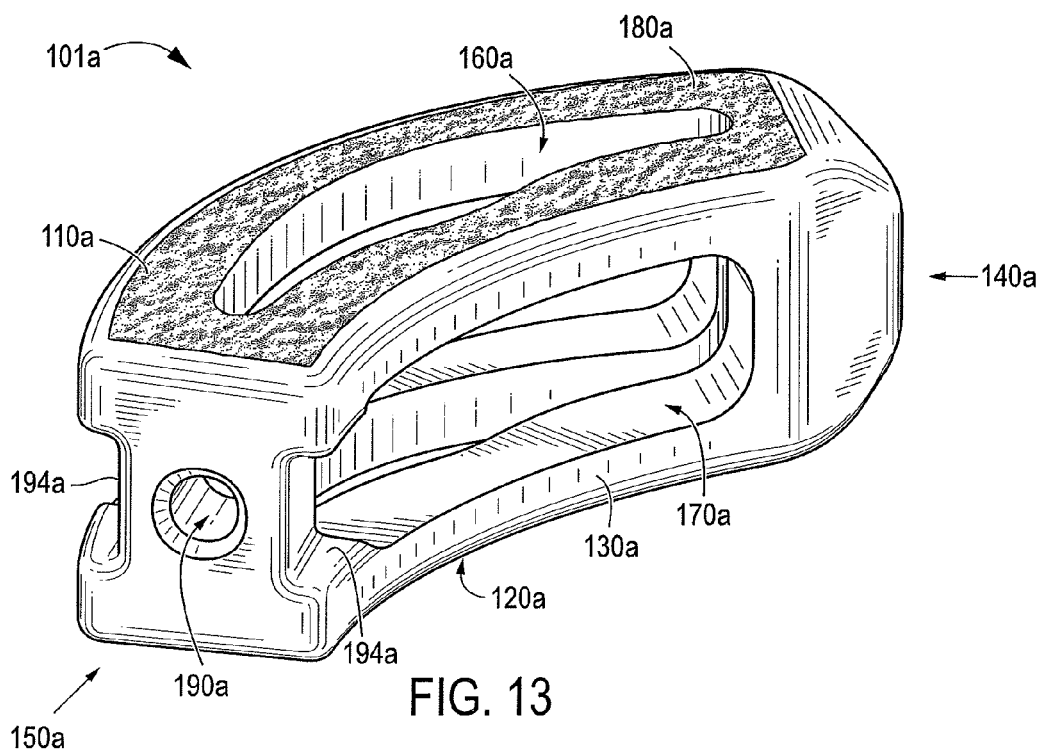
FIG. 13 shows a perspective view from the front of yet another embodiment of the interbody spinal implant according to the present invention.
Figure 14:
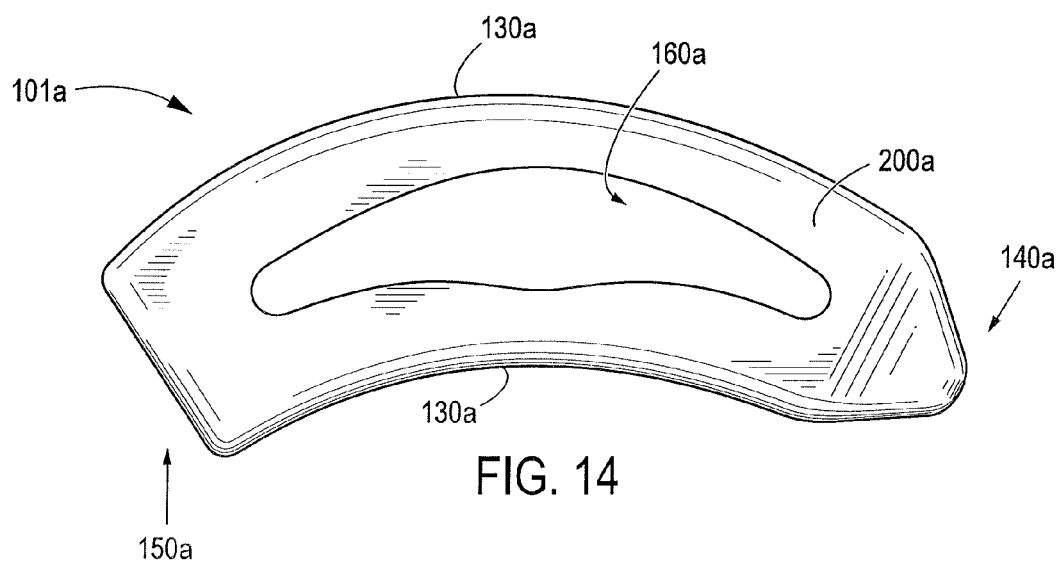
FIG. 14 is a top view of the interbody spinal implant illustrated in FIG. 13.
Figure 15:
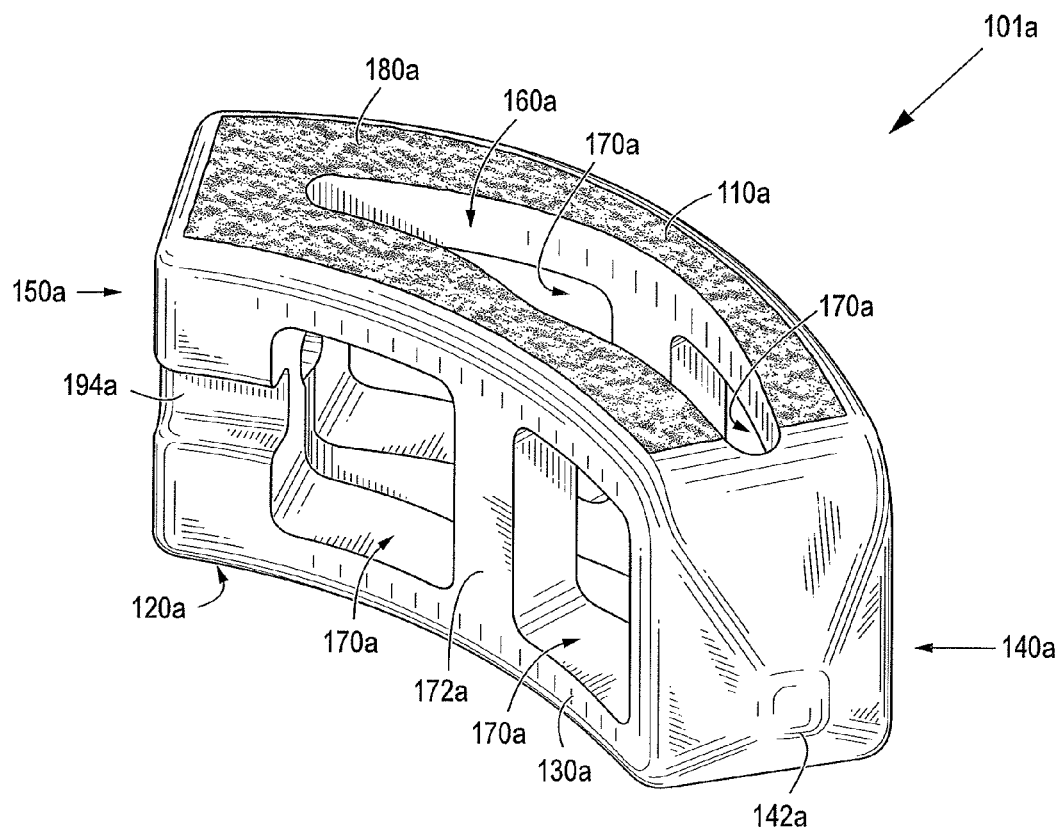
FIG. 15 shows a perspective view from the rear of the embodiment of the interbody spinal implant illustrated in FIG. 13 highlighting an alternative transverse aperture.

The embodiment of the present invention illustrated in FIGS. 13-15 is especially well suited when the spine surgeon elects a TLIF procedure. Many of the features of the implant 101*a* illustrated in FIGS. 13-15 are the same as those of the implant 101 illustrated in FIGS. 9-12. Therefore, these features are given the same reference numbers, with the addition of the letter "a," and are not described further.

There are several differences, however, between the two embodiments. For example, unlike the substantially rectangular shape of the implant 101, the implant 101*a* has a curved shape. Further, the chamfers 106 and sharp edges 108 of the implant 101 are replaced by curves or rounded edges for the implant 101*a*. Still further, the TLIF procedure often permits use of a larger implant 101*a* which, in turn, may affect the size and shape of the predetermined vertical aperture 160*a*.

The effect of the larger (relative to the implant 101) implant 101*a* is shown in FIG. 14, which illustrates a top view of the implant 101*a*. The substantially constant 9 mm width of the transverse rim 200 of the implant 101 is replaced with a larger, curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 200) allows the shape of the vertical aperture 160a to change, in cross section, from approximating a football to approximating a boomerang. Maintaining the thickness of the transverse rim 200a on either side of the vertical aperture 160a adjacent the center of the vertical aperture 160a at about 2 mm, similar to the dimensions of the implant 101, the center of the vertical aperture 160a, which defines the maximum width of the vertical aperture 160a, is increased (from 5 mm for the implant 101) to about 7 mm.

The implant 101a may also have a lordotic angle to facilitate alignment. As illustrated in FIG. 14, the lateral side 130a depicted at the top of the implant 101a is preferably generally greater in height than the opposing lateral side 130a. Therefore, the implant 101a may better compensate for the generally less supportive bone found in certain regions of the vertebral endplate.

As shown in FIG. 13, the transverse aperture 170a extends the entire transverse length of the implant body and nearly the entire height of the implant body. FIG. 15 highlights an alternative transverse aperture 170a. As illustrated in FIG. 15, the transverse aperture 170a is broken into two, separate sections by an intermediate wall 172a. Thus, the dimensions of the transverse aperture 170a shown in FIG. 15 are much smaller than those for the transverse aperture 170a shown in FIG. 13. The two sections of the alternative transverse aperture 170a are each illustrated as substantially rectangular in shape and extending nearly the entire height of the implant body; other sizes and shapes are possible for one or both sections of the alternative transverse aperture 170a.

The intermediate wall 172a may be made of the same material as the remainder of the implant 101a (e.g., metal), or it may be made of another material (e.g., PEEK) to form a composite implant 101a. It is also possible to extend the intermediate wall 172a, whether made of metal, PEEK, ultra-high molecular weight polyethylene (UHMWPE), or another material, to eliminate entirely the transverse aperture 170a. Given the reinforcement function of the intermediate wall 172a, the length of the vertical aperture 160a can be extended (as shown in FIG. 15) beyond the top surface 110a and into the anterior portion 140a of the implant 101a.

Also important is that the top surface 110a of the implant 101a shown in FIG. 14 differs from the top surface 110a of the implant 101a shown in FIGS. 13 and 15 in that the former does not include the roughened topography 180a of the latter. This difference permits the implant 101a, at least for certain applications, to be made entirely of a non-metal material. Suitable materials of construction for the implant 101a of such a design (which would not be a composite) include PEEK, hedrocel, UHMWPE, other radiolucent soft plastics, and additional materials as would be known to an artisan.

Figure 16:
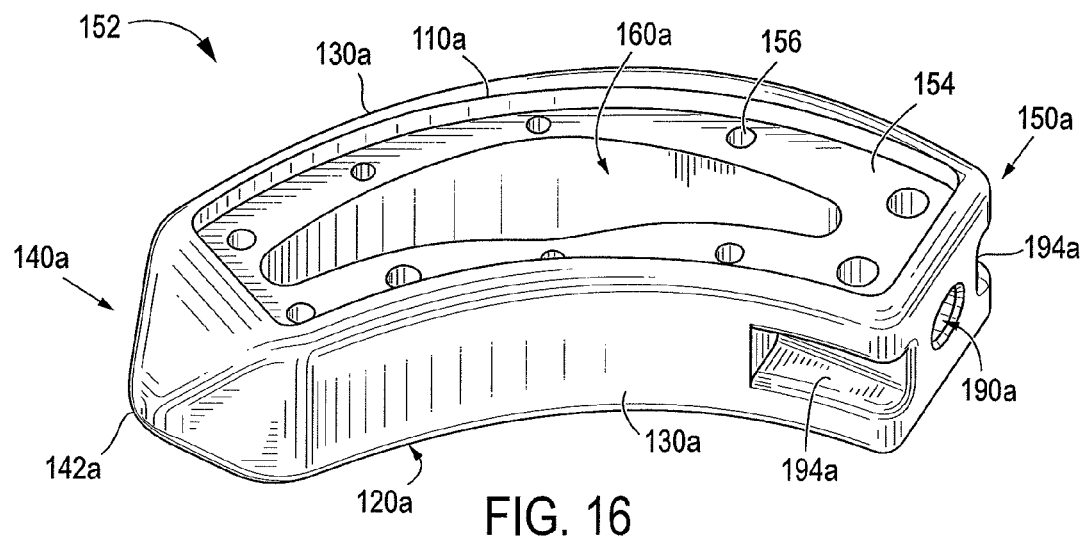
FIG. 16 shows a perspective view from the side of one component of a composite embodiment of the interbody spinal implant.
Figure 17:
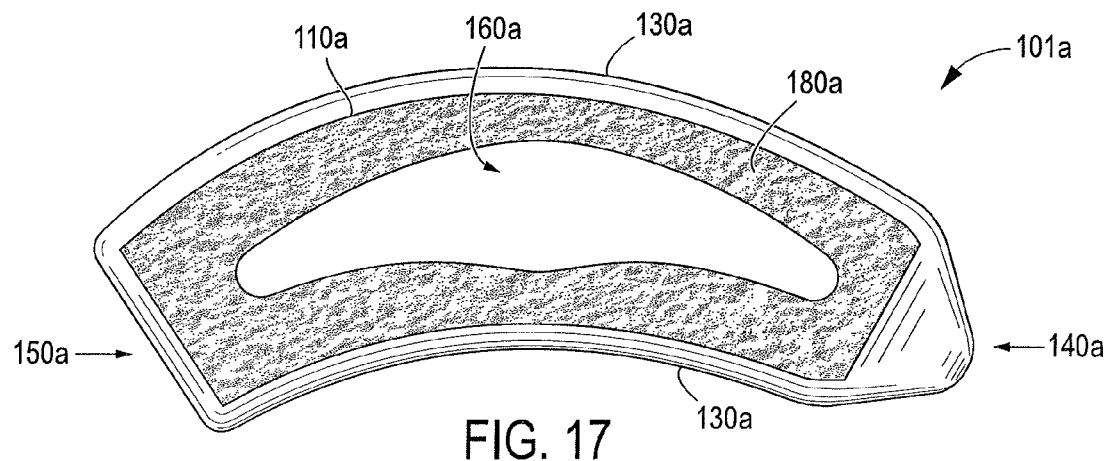
FIG. 17 is a top view of the composite embodiment of the interbody spinal implant illustrated in FIG. 16 with the components attached.

Another embodiment of a composite implant 101a is illustrated in FIGS. 16 and 17. FIG. 16 shows a perspective view from the side of one component of the composite implant 101a: an all plastic body 152. The body 152 may preferably be injection molded. PEEK is a suitable material for the body 152. In order to retain the advantages of a metal surface, including strength and an acid-etched roughened topography 180a, a second component of the composite implant 101a is provided: one or more metal strips or plates 162. The plates 162 may be provided on the top surface 110a, on the bottom surface 120a, or on both surfaces 110a and 120a.

Thus, the composite implant 101a combines the benefits of two, separate components: a body 152 and a plate 162. The composite structure of implant 101a advantageously permits the engineering designer of the implant 101a to balance the mechanical characteristics of the overall implant 101a. This allows the implant 101a to achieve the best balance, for example, of strength, resistance to subsidence, and stress transfer to bone graft. Moreover, although it is a relatively wide device designed to engage the ends of the vertebrae, the implant 101a can be inserted with minimal surgical modification. This combination of size and minimal surgical modification is advantageous.

The two components that form the composite implant 101a must be connected. As illustrated in FIG. 16, the body 152 of the composite implant 101a has a recessed upper surface 154. The recessed upper surface 154 is recessed below the top surface 110a of the composite implant 101a by an amount corresponding to the thickness of the plate 162 that will be installed over the recessed upper surface 154 to create a substantially flat top surface 110a. FIG. 17 is a top view of the composite interbody spinal implant 101a with the plate 162 installed. As illustrated in FIG. 17, the plate 162 has a roughened topography 180a. A corresponding second plate 162 may be installed on the bottom surface 120a of the composite implant 101a.

Figure 18:
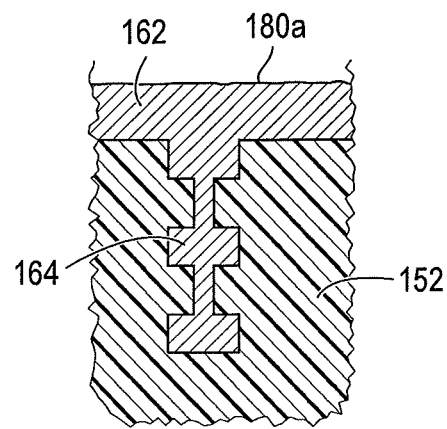
FIG. 18 shows an exemplary mechanism by which the two components of the composite embodiment of the interbody spinal implant illustrated in FIGS. 16 and 17 may be attached.

Any suitable connection mechanism, as would be known to an artisan, will suffice to install the plate 162 on the recessed upper surface 154 of the body 152. One connection mechanism is illustrated in FIGS. 16 and 18. FIG. 16 shows that a plurality of holes 156 are provided in the recessed upper surface 154 of the body 152. The holes 156 receive a corresponding plurality of legs 164 on the plate 162. The legs 164 are positioned on the plate 162 so that, when the plate 162 is installed over the recessed upper surface 154 of the body 152, each of the legs 164 engages one of the holes 156. Preferably, the legs 164 are integral with the remainder of the plate 162. By "integral" is meant a single piece or a single unitary part that is complete by itself without additional pieces, i.e., the part is of one monolithic piece formed as a unit with another part.

As shown in FIG. 18, the legs 164 may be configured to prevent them from exiting the holes 156. Thus, as shown, the legs 164 have a toothed periphery. If the plate 162 is metal and the body 152 is plastic, the body 152 may be injection molded around the legs 164 of the plate 162. In some applications, for example were the body 152 and the plate 162 both made of metal, it may be possible to provide corresponding threads on the legs 164 and holes 156.

The embodiments of the present invention described above are best suited for one or more of the ALIF, PLIF, and TLIF surgical procedures. Another embodiment of the present invention is better suited for cervical fusion procedures. This embodiment is illustrated in FIGS. 19 and 20 as the interbody spinal implant 201.

Because there is not a lot of disc material between the vertebral bodies in the cervical spine, the discs are usually not very large. The space available for the nerves is also not that great, however, which means that even a small cervical disc herniation may impinge on the nerve and cause significant pain. There is also less mechanical load on the discs in the cervical spine as opposed to the load that exists lower in the spine. Among others, these differences have ramifications for the design of the implant 201.

The implant 201 is generally smaller in size than the other implant embodiments. In addition, the lower mechanical load requirements imposed by the cervical application typically render a composite implant unnecessary. Therefore, the implant 201 is generally made entirely of metal (e.g., titanium) and devoid of other materials (e.g., PEEK).

Figure 19:
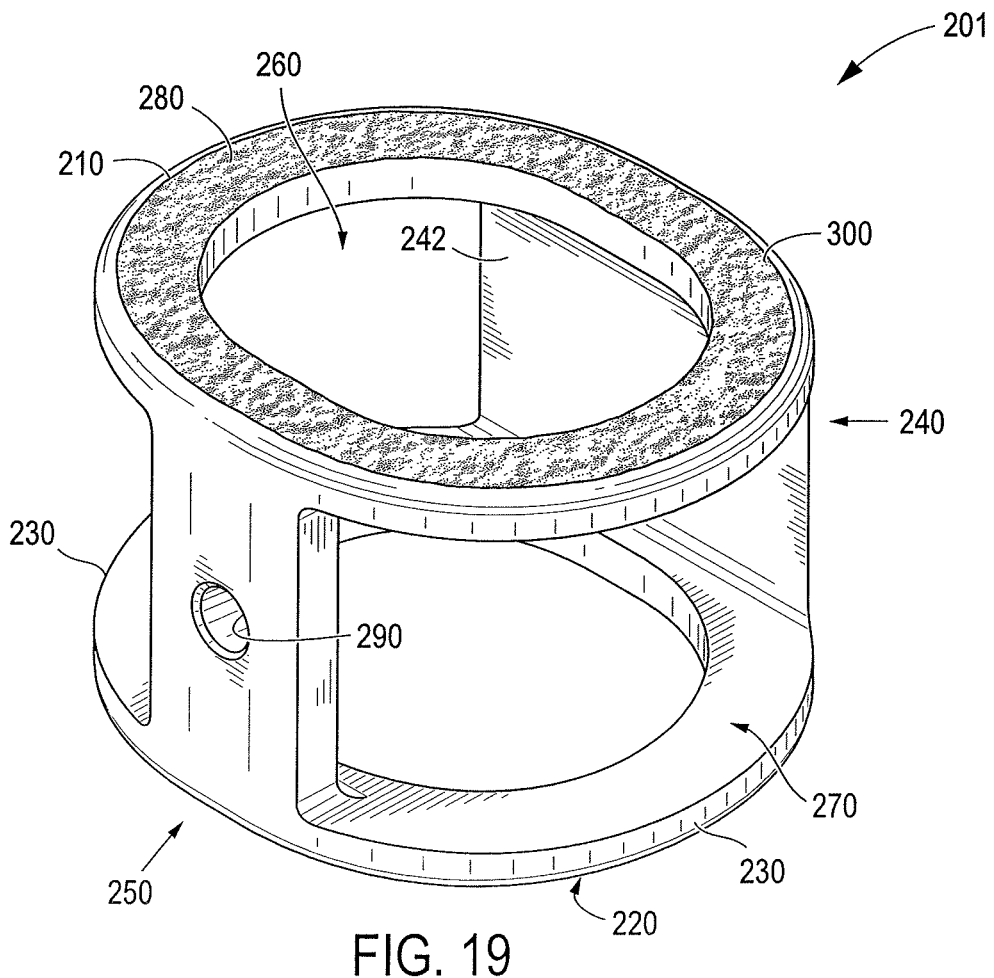
FIG. 19 shows a perspective view of a final embodiment of the interbody spinal implant having a generally oval shape and being especially well adapted for use in a cervical spine surgical procedure.
Figure 20:
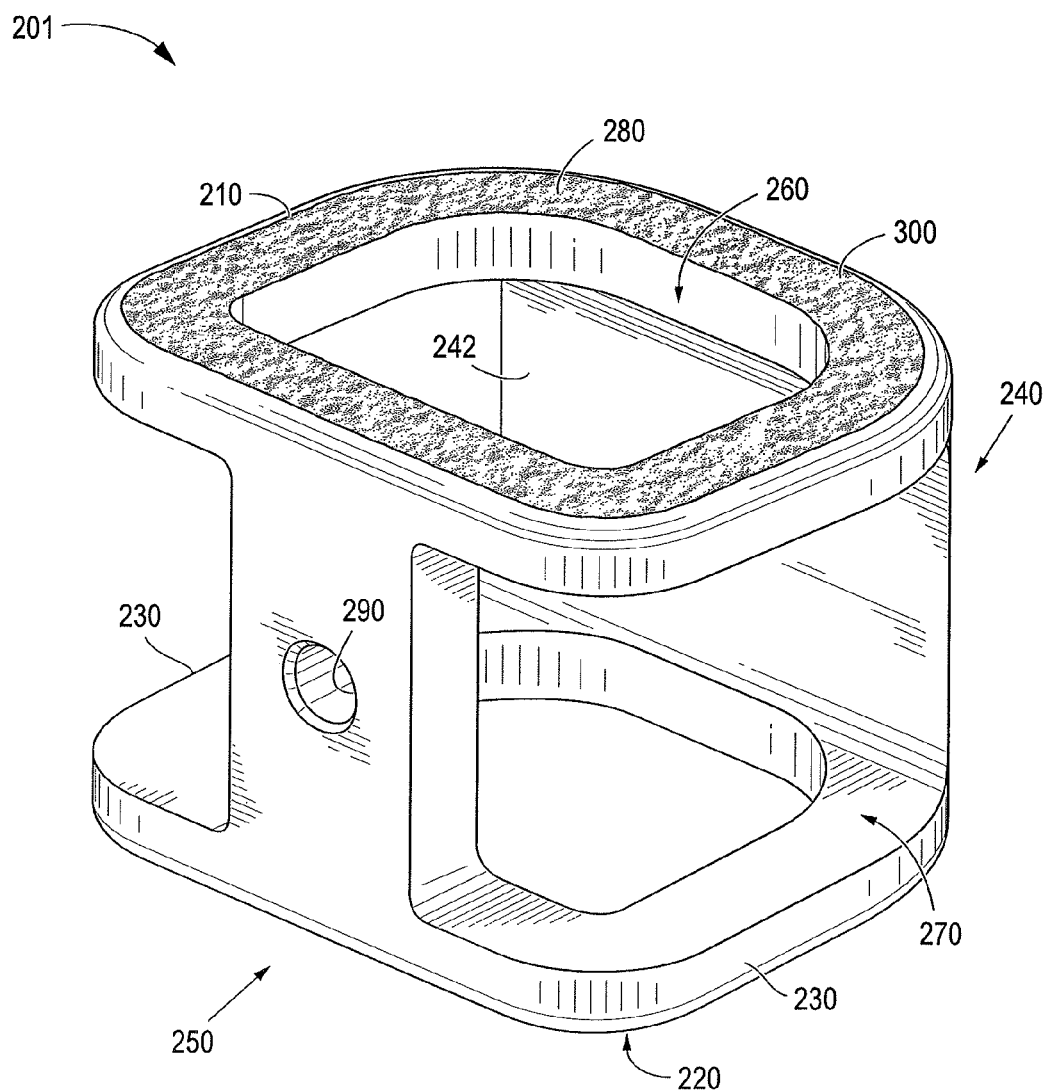
FIG. 20 shows a perspective view of the final implant having a generally box shape.

With specific reference to FIG. 19, the implant 201 includes a body having a top surface 210, a bottom surface 220, opposing lateral sides 230, and opposing anterior 240 and posterior 250 portions. One or both of the top surface 210 and the bottom surface 220 has a roughened topography 280 for gripping adjacent bone and inhibiting migration of the implant 201. The implant 201 is substantially hollow and has a generally oval shape with smooth, rounded, or both smooth and rounded edges.

The implant 201 includes at least one vertical aperture 260 that extends the entire height of the implant body. The vertical aperture 260 further defines a transverse rim 300. The size and shape of the vertical aperture 260 are carefully chosen to achieve a preferable design trade off for the particular application envisioned for the implant 201. Specifically, the vertical aperture 260 seeks to maximize the surface area of the top surface 210 and the bottom surface 220, to allow for better stress sharing between the implant 201 and the adjacent vertebral endplates, while maximizing access to the bone graft material provided within the implant 201. Thus, the size and shape of the vertical aperture 260 are predetermined by the application.

As illustrated in FIG. 19, the implant 201 has an opening 290 in the posterior portion 250. The opening 290 has a number of functions. One function is to facilitate manipulation of the implant 201 by the caretaker. Thus, the caretaker may insert a surgical tool (FIG. 6 shows an exemplary surgical tool, the implant holder 2) into the opening 290 and, through the engagement between the surgical tool and the opening 290, manipulate the implant 201. The opening 290 may be threaded to enhance the engagement.

The implant 201 may further include at least one transverse aperture 270. Like the vertical aperture 260, the size and shape of the transverse aperture 270 are carefully chosen (and predetermined) to achieve a preferable design trade off for the particular application envisioned for the implant 201. For example, as shown in FIG. 19, the transverse aperture 270 may extend the entire transverse length of the implant body and nearly the entire height of the implant body. Thus, the size and shape of the transverse aperture 270 approach the maximum possible dimensions for the transverse aperture 270.

As illustrated in FIG. 19, the implant 201 may be provided with a solid rear wall 242. The rear wall 242 extends the entire width of the implant body and nearly the entire height of the implant body. Thus, the rear wall 242 essentially closes the anterior portion 240 of the implant 201. The rear wall 242 may offer one or more of several advantages, including reinforcement of the implant 201 and improved bone graft containment. In the cervical application, it may be important to prevent bone graft material from entering the spinal canal.

Alternative shapes for the implant 201 are possible. As illustrated in FIG. 20, for example, the implant 201 may have a generally box shape which gives the implant 201 increased cortical bone coverage. Like the implant 201 shown in FIG. 19, the implant 201 shown in FIG. 20 has a curved transverse rim 300 in the area of the anterior portion 240. The shape of the posterior portion 250 of the implant 201 is substantially flat, however, and the shape of the transverse rim 300 in the area of the posterior portion 250 is substantially square. Thus, the posterior portion 250 provides a face that can receive impact from a tool, such as a surgical hammer, to force the implant 201 into position.

The implant 201 may also have a lordotic angle to facilitate alignment. As illustrated in FIGS. 19 and 20, the anterior portion 240 is preferably generally greater in height than the posterior portion 250. Therefore, the implant 201 may better compensate for the generally less supportive bone found in certain regions of the vertebral endplate. As an example, four degrees of lordosis may be built into the implant 201 to help restore balance to the spine. There are other shapes of this surface that may be advantageous, convex, concave and angled either to one side or the other.

Certain embodiments of the implant 1, 101, 101a, 101b (see below), and 201 are generally shaped (i.e., made wide) to maximize contact with the apophyseal rim of the vertebral endplates. They are designed to be impacted between the endplates, with fixation to the endplates created by an interference fit and annular tension. Thus, the implants 1, 101, 101a, 101b, and 201 are shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis (or more) may be built into the implants 1, 101, 101a, 101b, and 201 to help restore cervical balance.

When endplate-sparing spinal implant 1, 101, 101a, 101b, and 201 seats in the disc space against the apophyseal rim, it should still allow for deflection of the endplates like a diaphragm. This means that, regardless of the stiffness of the spinal implant 1, 101, 101a, 101b, and 201, the bone graft material inside the spinal implant 1, 101, 101a, 101b, and 201 receives load, leading to healthy fusion. The vertical load in the human spine is transferred though the peripheral cortex of the vertebral bodies. By implanting an apophyseal-supporting inter-body implant 1, 101, 101a, 101b, and 201, the natural biomechanics may be better preserved than for conventional devices. If this is true, the adjacent vertebral bodies should be better preserved by the implant 1, 101, 101a, 101b, and 201, hence reducing the risk of adjacent segment issues.

In addition, the dual-acid etched roughened topography 80, 180, 180a, and 280 of the top surface 30, 130, 130a, and 230 and the bottom surface 40, 140, 140a, and 240 along with the broad surface area of contact with the end-plates, is expected to yield a high pull-out force in comparison to conventional designs. As enhanced by the sharp edges 8 and 108, a pull-out strength of up to 3,000 nt may be expected. The roughened topography 80, 180, 180a, and 280 creates a biological bond with the end-plates over time, which should enhance the quality of fusion to the bone. Also, the in-growth starts to happen much earlier than the bony fusion. The center of the implant 1, 101, 101a, 101b, and 201 remains open to receive bone graft material and enhance fusion. Therefore, it is possible that patients might be able to achieve a full activity level sooner than for conventional designs.

The spinal implant 1, 101, 101a, 101b, and 201 according to the present invention offers several advantages relative to conventional devices. Such conventional devices include, among others, ring-shaped cages made of allograft bone material, threaded titanium cages, and ring-shaped cages made of PEEK or carbon fiber. Several of the advantages are summarized with respect to each conventional device, in turn, as follows.

1. Advantages Over Allograft Bone Material Cages

The spinal implant 1, 101, 101a, 101b, and 201 is easier to use than ring-shaped cages made of allograft bone material. For example, it is easier to prepare the graft bed, relative to the allograft cage, for the spinal implant 1, 101, 101a, 101b, and 201. And ring allograft cages typically are not sufficiently wide to be implanted on the apophasis. The spinal implant 1, 101, 101a, 101b, and 201 offers a large internal area for bone graft material and does not require graft preparation, cutting, or trimming. The central aperture 60, 160, 160a, and 260 of the spinal implant 1, 101, 101a, 101b, and 201 can be filled with cancellous allograft, porous synthetic bone graft substitute (such as the material offered by Orthovita, Inc., Malvern, Pa., under the Vitoss trademark), or BMP. The process of healing the bone can proceed by intra-membranous ossification rather than the much slower process of enchondral ossification.

The spinal implant 1, 101, 101a, 101b, and 201 is generally stronger than allograft cages. In addition, the risk of osteolysis (or, more generally, disease transmission) is minimal with the spinal implant 1, 101, 101a, 101b, and 201 because titanium is osteocompatible. The titanium of the spinal implant 1, 101, 101a, 101b, and 201 is unaffected by BMP; there have been reports that BMP causes resorption of allograft bone.

2. Advantages Over Threaded Titanium Cages

In contrast to conventional treaded titanium cages, which offer little bone-to-bone contact (about 9%), the spinal implant 1, 101, 101a, 101b, and 201 has a much higher bone-to-bone contact area and commensurately little metal-to-bone interface. Unlike threaded titanium cages which have too large a diameter, the spinal implant 1, 101, 101a, 101b, and 201 can be relatively easily used in "tall" disc spaces. The spinal implant 1, 101, 101a, 101b, and 201 can also be used in either a "stand alone" manner in collapsed discs or as an adjunct to a 360-degree fusion providing cervical column support.

The spinal implant 1, 101, 101a, 101b, and 201 offers safety advantages over conventional threaded titanium cages. The spinal implant 1, 101, 101a, 101b, and 201 is also easier to implant, avoiding the tubes necessary to insert some conventional cages, and easier to center. Without having to put a tube into the disc space, the vein can be visualized by both the spine surgeon and the vascular surgeon while working with the spinal implant 1, 101, 101a, 101b, and 201. Anterior-posterior (AP) fluoroscopy can easily be achieved with trial before implanting the spinal implant 1, 101, 101a, 101b, and 201, ensuring proper placement. The smooth and rounded edges of the spinal implant 1, 101, 101a, 101b, and 201 facilitate insertion and enhance safety. No reaming of the endplate, which weakens the interface between the endplate and the cage, is necessary for the spinal implant 1, 101, 101a, 101b, and 201. Therefore, no reamers or taps are generally needed to insert and position the spinal implant 1, 101, 101a, 101b, and 201.

3. Advantages Over PEEK/Carbon Fiber Cages

Cages made of PEEK or carbon fiber cannot withstand the high impact forces needed for implantation, especially in a collapsed disc or spondylolisthesis situation, without secondary instruments. In contrast, the spinal implant 1, 101, 101a, and 201 avoids the need for secondary instruments. Moreover, relative to PEEK or carbon fiber cages, the spinal implant 1, 101, 101a, 101b, and 201 provides better distraction through endplate sparing and being designed to be implanted on the apophysis (the bony protuberance of the human spine). The titanium of the top surface 10, 110, 110a, and 210 and the bottom plate 20, 120, 120a, and 220 of the spinal implant 1, 101, 101a, 101b, and 201 binds to bone with a mechanical (knawling) and a chemical (a hydrophilic) bond. In contrast, bone repels PEEK and such incompatibility can lead to locked pesudoarthrosis.

EXAMPLE SURGICAL METHODS

The following examples of surgical methods are included to more clearly demonstrate the overall nature of the invention. These examples are exemplary, not restrictive, of the invention. Certain embodiments of the present invention are particularly suited for use during interbody spinal implant procedures currently known in the art. The methods according to the present invention minimize, if they do not eliminate, the cutting of bone. The methods can be described as including three, main steps, each of which includes several substeps.

Step I

1. The disc space is accessed using a standard mini-open retroperitoneal laparotomy.

2. The center of the disc space is located by AP fluoroscopy, making sure the pedicles are equidistant from the spinous process.

3. The disc space is incised by making a window in the annulus for insertion of certain embodiments of the spinal implant 1, 101, 101a, 101b, and 201. A 28, 32, or 36 mm window in the annulus is typically suitable for device insertion. The pre-determined width of the window should be about 4 mm smaller than the mid-line width of the implant 1, 101, 101a, 101b, and 201 to be inserted. The annulus is the connecting tissue that circumferential encapsulates the disc and is preserved as part of the surgical method. The instruments and implants have smoothed and rounded entry faces on the anterior and most outer surfaces that reduce friction upon insertion into the inter-disc space. The implants 1, 101, 101a, 101b, and 201 have a sufficiently "sharp" trailing edge, which resists expulsion. The instruments have connection points for long handles that also have smoothed or polished surfaces and rounded edges.

4. The endplates are cleaned of all cartilage with a curette. The disc structure which is encapsulated by the annulus is removed. As part of the endplate-preserving method, care is taken to not damage the endplate structure of the vertebrae. Removal of the soft connective tissues that comprise the annulus is also avoided as much as possible where undamaged by the medical condition of the patient.

5. A size-specific rasp (or broach) 14 may then be used. For anterior methods where the implant 1, 101, 101a, 101b, and 201 is inserted from the front of the patient through the abdominal cavity, rasp instruments are provided in implant sizes and heights. Rasps 14 have rounded edges in areas where they are not intended to contact the endplates and these faces are significantly smooth or polished. Teeth are located on the opposing top and bottom surfaces and have tooth profile designs that are not overly aggressive and face the direction of removal to aid is removing the disc material. Their primary purpose on anterior procedures is to complete the cleaning of the disc, especially in the posterior lateral corners where access is limited. This facilitates positioning of the implant 1, 101, 101a, 101b, and 201 aligned with the apophyseal ring structure of the vertebrae. This also allows for the wider integration surface area of the implant 1, 101, 101a, 101b, and 201 to be seated in a region of the spinal column where the largest amount of load transfers through the disc space. Spreading these loads over this larger area reduces the potential for stress-induced necrosis of the opposing biologic structures.

Figure 8:
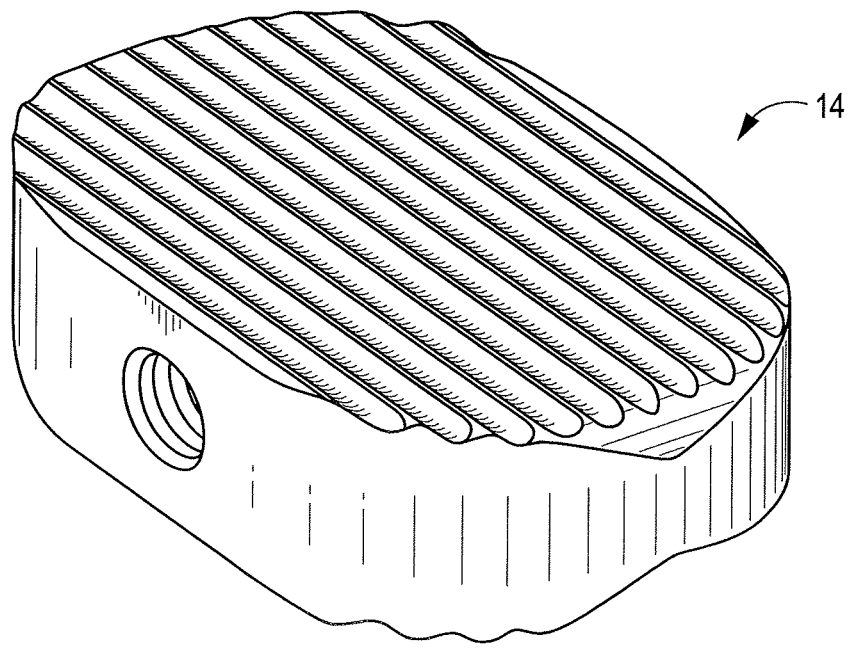
FIG. 8 shows an exemplary rasp used during certain methods of implantation.

FIG. 8 shows an exemplary rasp 14 used during certain methods of implantation. Typically, a 28 mm or a 32 mm or a 36 mm rasp 14 is used. A single rasp 14 is used to remove a minimal amount of bone. A lateral C-arm fluoroscopy can be used to follow insertion of the rasp 14 in the posterior disc space. The smallest height rasp 14 that touches both endplates (e.g., the superior and inferior endplates) is first chosen. After the disc space is cleared of all soft tissue and cartilage, distraction is then accomplished by using distractors (also called implant trials or distraction plugs) as described below. It is usually possible to distract 2-3 mm higher than the rasp 14 that is used because the disc space is elastic.

Use of a size-specific rasp 14, as shown in FIG. 8, preferably minimizes removal of bone, thus minimizing impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant 1, 101, 101a, 101b, and 201 is to be seated near the center of the vertebral endplate or the implant 1, 101, 101a, 101b, and 201 is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant 1, 101, 101a, 101b, and 201 into the vertebral body.

Step II

6. Lateral C-arm fluoroscopy is used to follow the insertion of the rasp 14 into the posterior disc space. Anterior rasps 14 can be disconnected from the handle instrument to facilitate viewing and reconnected for further tissue removal or removal of the rasp 14 itself. There are also instruments that allow for reaching into the interbody space and moving the position of the instruments using impact loads. The handles and pushers have a rigid shaft design with a metal core that connects the end of the handle to the tip allowing for durability and directed impacting without damage to the instrument. Further instruments can be connected to the handle instruments that can concentrate impact loading for insertion and removal of the rasp and distractor instruments as well as the implant 1, 101, 101a, 101b, and 201.

7. All instruments and implants are designed with significantly rigid materials, structures, and geometric shapes to allow for rigorous loading during implantation. The amount of force that can be applied to the instruments and implants far exceeds the structural requirements of an interbody device as it would be biologically loaded by the patient. This design consideration allows for the rigorous surgical method to assure a frictional fit of the implant 1, 101, 101a, 101b, and 201 into the disc space without risking damage to the implant 1, 101, 101a, 101b, and 201 as is seen in designs where the implant is fabricated solely from polymers or autograft (harvested bone) materials. The implant 1, 101, 101a, 101b, and 201 is unique in the fact that both distraction and reduction of deformity may be achieved without additional instruments.

8. As noted above, the smallest height rasp 14 that touches both endplates is chosen first. As part of the design of the rasps 14, these instruments have a fit relationship with the distraction instruments and the implant 1, 101, 101a, 101b, and 201 that assures that when the implant 1, 101, 101a, 101b, and 201 is placed it achieves a friction fit into the prepared disc space and is stabilized for healing and fusion of the two contacted bones. This fit relationship is set through sequential placement of the distractors. The surgical method includes testing the elongation of the annulus connection to the discs by observing the elongation and condition of annulus tissue structure. The goal is to tension the annulus, but not over stress it or damage it.

9. The instruments are designed to be endplate sparing. More specifically, the instruments are designed to remove the cartilaginous endplate but preserve the strongest portion of the endplate as well as the arch. Sizing and placement of the implant 1, 101, 101a, 101b, and 201 on the periphery of the vertebral endplate allows proper loading of the implant 1, 101, 101a, 101b, and 201 and graft, and, therefore, limits subsidence.

10. After disc space is cleared of all soft tissue and cartilage, movement of the two opposing vertebrae is then accomplished by using distractors 12. Distractors 12 are a polished disc in the shape of the implant 1, 101, 101a, 101b, and 201 with heights that correspond to the sizes of the implants 1, 101, 101a, 101b, and 201. The distractors 12 also can have a connection that allows for a handle instrument to be assembled to them and they in turn can be impacted using other provided instruments to position them correctly within the disc space. The connections and structures of the distractors 12 are large enough to withstand impact loading, but balanced to allow for access into the surgical site past the delicate structures of the spine and vascular system. When the methods are conducted through the anterior approach, major blood vessels are retracted to allow for access and in order to aid in the protection of these vessels the distractors 12 and handles are polished with smooth surfaces to minimize risk of abrasion damage. The distractors 12 also have large radii on leading and trailing surfaces that contact the endplates so as to preserve the bone structures of the vertebrae. Size identifications are prominently marked on the rasps 14 and distractors 12 to aid in selection of the preferred implant footprint and height.

Figure 7:
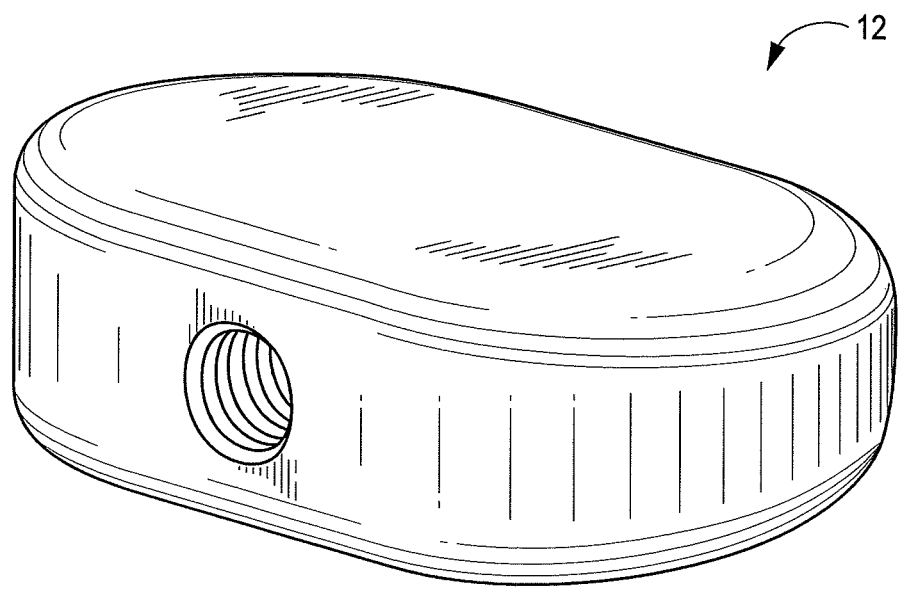
FIG. 7 shows an exemplary distractor used during certain methods of implantation.

FIG. 7 shows an exemplary distractor 12 used during certain methods of implantation. The implant trials, or distractors 12, are solid polished blocks which have a peripheral geometry identical to that of the implant 1, 101, 101a, 101b, and 201. These distractor blocks may be made in various heights to match the height of the implant 1, 101, 101a, 101b, and 201. The disc space is adequately distracted by sequentially expanding it with distractors 12 of progressively increasing heights. The distractor 12 is then left in the disc space and the centering location may be checked by placing the c-arm back into the AP position. If the location is confirmed as correct (e.g., centered), the c-arm is turned back into the lateral position. The spinal implant 1, 101, 101a, 101b, and 201 is filled with autologous bone graft or bone graft substitute. The distractor 12 is removed and the spinal implant 1, 101, 101a, 101b, and 201 is inserted under c-arm fluoroscopy visualization. The process according to the present invention may not use a secondary distractor; rather, distraction of the disc space may be provided by the spinal implant 1, 101, 101a, 101b, and 201 itself (i.e., the implant 1, 101, 101a, 101b, and 201 itself is used as a distractor).

11. Size selection of the implant 1, 101, 101a, 101b, and 201 is accomplished through inserting taller distractors 12 which are provided in incremental sizes and often can be 2-5 mm higher than the rasp 14 that is initially used. Imaging of the distractors 12 can be conducted if required, but the amount of tension on the annulus and the retention in the prepared site is also tested by the surgeon to determine the correct or desired balance of frictional fit and elongation of the annulus. The lack of teeth to achieve initial stability preserves the integrity of the endplate, and therefore limits subsidence.

Step III

12. The distractor 12 is left in disc space and its relationship to the centerline of the vertebra is checked in two view planes from the front and sides of the patient.

13. The size of the last distraction defines the correct size of the implant 1, 101, 101a, 101b, and 201 to be implanted. The implant 1, 101, 101a, 101b, and 201 may be larger than the last distractor 12 by about 1 mm in height if a tighter fit is desired.

14. The implant 1, 101, 101a, 101b, and 201 is packed with autograft bone prior to placement in the site. Windows in the implant 1, 101, 101a, 101b, and 201 passing from anterior-to-posterior and laterally across the implant 1, 101, 101a, 101b, and 201 allow for loading of graft materials before placement and can also serve as access points once the implant 1, 101, 101a, 101b, and 201 is seated. The large windows also facilitate additional graft packing post-insertion to allow packing into the arch of the endplates. A solid back wall on the implant 1, 101, 101a, 101b, and 201 can prevent migration of bone graft toward the spinal cord.

15. The central axial openings of the implant 1, 101, 101a, 101b, and 201 allow for contact of the graft material to the endplate structures. Endplate structures can change shape during biologic loading and the resulting pressure is conducted through the graft materials stimulating growth of bone tissues within the implant 1, 101, 101a, 101b, and 201. Surfaces of the implants 1, 101, 101a, 101b, and 201 are treated to enhance the biological activities within the healing fusion. Without being limited by theory it is believed that, at the microscopic level, the treatment methods stimulate specific responses and coupled with the a-traumatic surgical method, preserving the endplates, the frictional stability, and the roughened integration surface of the implant 1, 101, 101a, 101b, and 201 yield significant improvements in the fusion rates and bone quality.

16. The implant 1, 101, 101a, 101b, and 201 is easily inserted and seated under C-arm fluoroscopic visualization. Such visualization is another intended design feature in the implants 1, 101, 101a, 101b, and 201 where the windows into the central hollow core of the implant 1, 101, 101a, 101b, and 201 are as large as possible but are shaped to maximize structural integrity of the implant 1, 101, 101a, 101b, and 201. These windows are also aligned across the central axis of the implant 1, 101, 101a, 101b, and 201 to allow for visualization of the growing fusion column of patient bone during the healing process.

The instrument connection features of the implant 1, 101, 101a, 101b, and 201 are designed with adequate rigidity and structure to withstand the required impacting to seat the implant 1, 101, 101a, 101b, and 201 in the joint space. The implant 1, 101, 101a, 101b, and 201 used in concert with minimal instrumentation and following a bone-preserving surgical technique simplifies and speeds completion of disk replacement surgical procedures. The present invention balances the method of use and the structure of the implant 1, 101, 101a, 101b, and 201 to assure controlled impacting and correct seating in the site. Enhanced surfaces of the implant 1, 101, 101a, 101b, and 201 stimulate without additional medications the natural bone growth activities that occur during the fusion of the implant 1, 101, 101a, 101b, and 201 into the joint. The ability to move or distract the joint space into a biologically correct relationship is enhanced by the balanced surface area, the roughened surface of the implant 1, 101, 101a, 101b, and 201, and the treatment of the surface through various processes that combine to improve initial stability and, during the healing process, fusion of the two separate bones in the joint.

Figure 21:
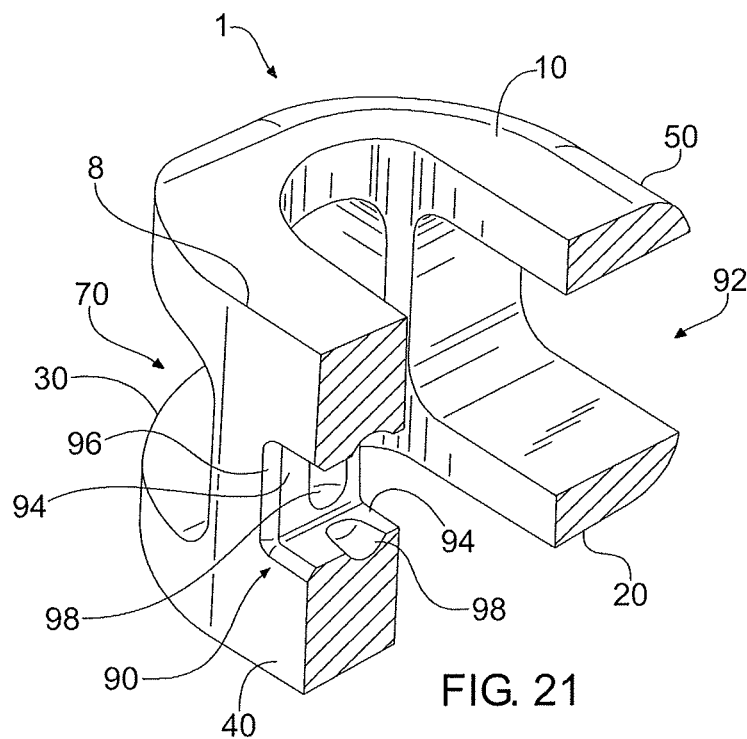
FIG. 21 shows a cross-sectional view of the interbody spinal implant having the shape of the first embodiment illustrated in FIG. 1.
Figure 22:
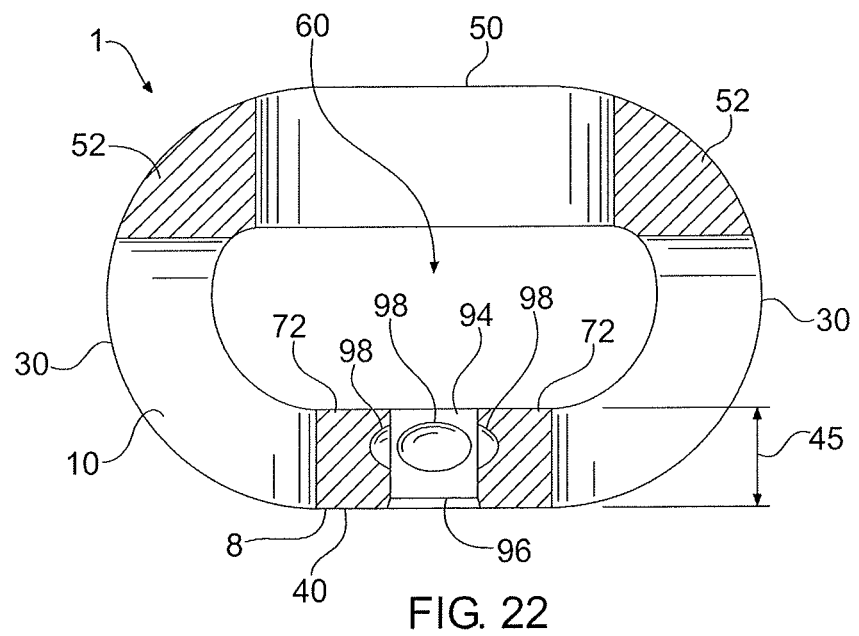
FIG. 22 shows a top view of the interbody spinal implant illustrated in FIG. 21.

The instrument connection features of the implant 1, 101, 101a, 101b, and 201 are now highlighted. FIGS. 21 and 22 show a cross-sectional view and a top view, respectively, of the interbody spinal implant 1 (without certain features such as the roughened topography 80). As illustrated in FIGS. 1, 21, and 22, the implant 1 has an opening 90 in the anterior portion 40. The caretaker may insert a surgical tool or instrument into the opening 90 and, through the engagement between the instrument and the opening 90, manipulate the implant 1.

The opening 90 may have any one of a number of geometric shapes, including square, rectangular, round, oval, and the like. As illustrated in FIGS. 21 and 22, the opening 90 is a square formed of four equal faces 94. Each face 94 is about 5 mm long in one embodiment. A transition is provided from the anterior 40 to the opening 90 by a radiused insertion feature 96. As illustrated in FIGS. 21 and 22, the radiused insertion feature 96 is a chamfer. Each of the four chamfers that comprise the radiused insertion feature 96 of the embodiment illustrated are 0.8 mm wide and at an angle of 45 degrees. A function of the radiused insertion feature 96 is to facilitate (i.e., guide) insertion by the caretaker of the instrument into the opening 90. The radiused insertion feature 96 also allows for off-axis adjustments by the caretaker.

The opening 90 has an instrument retention feature 98 to help retain the implant holder 2 (or other instrument), which the caretaker uses to manipulate the implant 1, in connection with the implant 1. The instrument retention feature 98 may be any one of a number of features, including a thread (as discussed below) or a notch (as shown in FIGS. 21 and 22). As shown, each face 94 has an oval-shaped notch.

Preferably, the opening 90 is centrally positioned in the anterior 40 of the implant 1. As shown in FIG. 21, for the embodiment illustrated, the distance from the edge of one transverse aperture 70 to the face 94 of the opening 90 nearest that one transverse aperture 70 is about 3.6 mm. The distance (not shown) from the edge of the opposite transverse aperture 70 to the face 94 of the opening 90 nearest that opposite transverse aperture 70 is also about 3.6 mm. Thus, the opening 90 is disposed centrally between the opposing transverse apertures 70.

Similarly, and as shown in FIG. 21 for the embodiment illustrated, the distance from the bottom surface 20 to the face 94 of the opening 90 nearest that bottom surface 20 is about 5.8 mm. The distance from the top surface 10 to the face 94 of the opening 90 nearest that top surface 10 is also about 5.8 mm. Thus, the opening 90 is disposed centrally between the top surface 10 and the bottom surface 20.

Several functional advantages are achieved by centrally positioning the opening 90 in the anterior 40 of the implant 1. First, the surgical tool or instrument that engages the opening 90 is centered, which facilitates a centered movement of the implant 1 using the instrument. In other words, the centered opening 90 minimizes the risk that force applied to the implant 1 through the instrument will push the implant 1 off axis or skew the implant 1 during insertion. The centered opening 90 also allows the caretaker to impart the maximum force to the implant 1, using the instrument, along the midline of the implant 1.

FIG. 22 shows that the illustrated embodiment of the implant 1 has four structural columns 52, 72. The term "structural column" defines an integral, solid, unitary part of the implant 1 that is uninterrupted by an opening or aperture. In other words, the part is integral from the top surface 10 to the bottom surface 20. Two structural columns 52 are disposed on opposite sides of the alternative opening 92, forming the junctions between the posterior 50 and the opposing lateral sides 30. Two additional structural columns 72 are disposed on opposite sides of the opening 90, between the opening 90 and the opposing transverse apertures 70. The structural columns 52, 72 give the implant 1 rigidity and strength. Such rigidity and strength are especially important for structural columns 72, which form part of the anterior 40, because the anterior 40 forms an impact face. The large, flat area of the anterior 40 can be impacted by an instrument to drive or move the implant 1 into a desired surgical position.

FIG. 22 includes several example dimensions for the embodiment of the implant 1 illustrated. The length of each structural column 72 along the anterior 40 of the implant 1 is about 3.6 mm and the anterior thickness 45 (i.e., the depth of each structural column 72 from the anterior 40 to the aperture 60) is about 5 mm. Note the corresponding dimensions illustrated in FIG. 21 and discussed above. The length of each structural column 52, at the juncture between the structural column 52 and the lateral side 30, is about 5.6 mm. The depth of each structural column 52, at the juncture between the structural column 52 and the posterior 50, is about 6.4 mm. These example dimensions are highlighted in areas where structural durability is required for the implant 1 to sustain impact loading and to facilitate manipulation during implantation.

Figure 23:
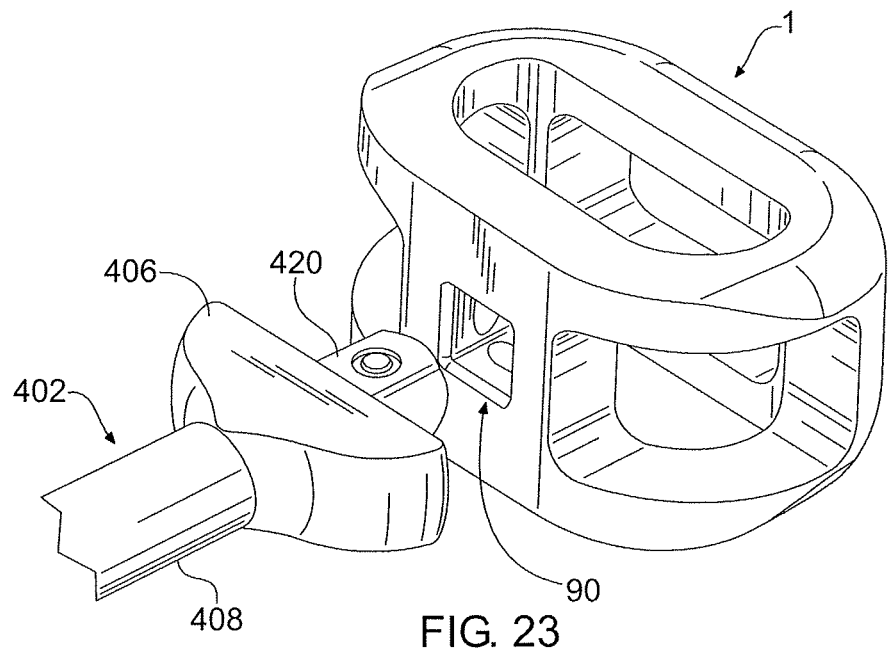
FIG. 23 shows a portion of an instrument adapted to engage with and manipulate the implant illustrated in FIGS. 21 and 22.
Figure 25:
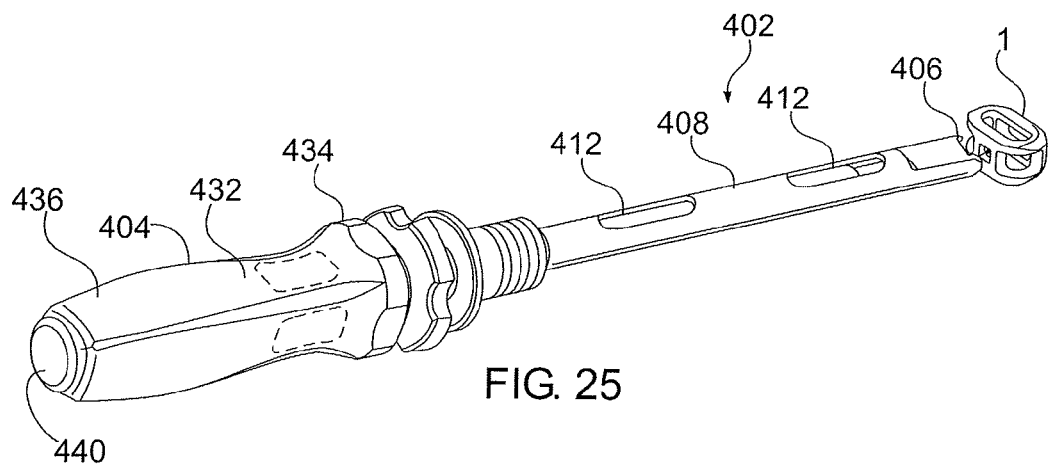
FIG. 25 shows an instrument adapted to engage with and manipulate the implant according to another embodiment of the present invention.

As discussed above in connection with FIG. 6, the caretaker can use the implant holder 2 to engage and manipulate the implant 1. FIG. 23 shows a portion of an instrument 402, adapted to engage with and manipulate the implant 1, for alternative use by the caretaker. The instrument 402 has a rigid shaft 408 connected to (and preferably integral with) a rigid and durable handle 404 (see FIG. 25). The shaft 408 may be solid or, as shown in FIG. 25, may have one or more slots 412. The slots 412 reduce the weight of the shaft 408, facilitate visualization, and can impart other information such as how far the implant 1 has been inserted into a patient. On its end opposite the handle 404, the shaft 408 is connected to (and preferably integral with) an impact head 406.

Figure 24:
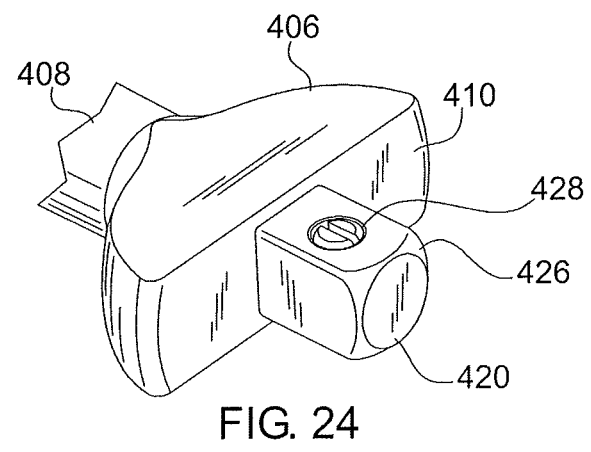
FIG. 24 highlights the impact head of the instrument shown in FIG. 23.

FIG. 24 highlights the impact head 406 of the instrument 402 shown in FIG. 23. The impact head 406 has a flat impact face 410. A projection 420 extends from the impact face 410 perpendicularly away from the impact face 410. The projection 420 is disposed centrally on the impact face 410, and is preferably axially aligned with the shaft 408. Such disposition and alignment facilitate transfer of forces from the impact head 406 to the implant 1. The impact face 410 contacts the anterior 40 of the implant 1, with the projection 420 inserted into the opening 90 of the implant 1, when the caretaker engages the instrument 402 with the implant 1. Thus, the majority of the forces transmitted from the instrument 402 to the implant 1 are transmitted by the implant face 410 to the anterior 40.

The projection 420 has a plurality of chamfers 426. The chamfers 426 correspond to the radiused insertion features 96 of the implant 1 to facilitate (i.e., guide) insertion of the projection 420 into the opening 90. The projection 420 also has one or more nubs 428. The nubs 428 correspond to the instrument retention features 98 of the implant 1 to facilitate engagement between the instrument 402 and the implant 1. More specifically, the nubs 428 engage the instrument retention features 98 upon insertion of the projection 420 into the opening 90. The corners of the projection 420 allow for rotation of the implant 1 in off-axis directions, allowing the caretaker to adjust the position of the implant 1 when the implant 1 is positioned between vertebrae of a patient. Note that none of the components illustrated in FIGS. 21-24 are threaded.

Example dimensions for the impact head 406 vary, of course, to correspond to the dimensions of the implant 1 which the instrument 402 will engage. For the implant 1 illustrated in FIGS. 21 and 22, the width of the impact face 410 on opposite sides of the projection is about 7.1 mm. The width of the projection 420 is about 4.7 mm. Because the projection 420 is square, the height of the projection 420 is also about 4.7 mm. The diameter of the shaft is about 6.4 mm.

The caretaker can easily grasp and manipulate the instrument 402 using the handle 404. As shown in FIG. 25, the handle 404 may have a number of ergonomic features to facilitate such grasping and manipulation. Among these ergonomic features are curved indentations 432 for contact by the fingers of the caretaker; a rim 434 for contact by the forward portion of the hand of the caretaker; a bulbous portion 436 for contact by the palm of the caretaker; and surfaces that are smooth, relatively soft, and comfortable for contact by the skin of the caretaker. These and other ergonomic features are well known in the art and are within the knowledge of the artisan.

The handle 404 also has a cap 440 on its end opposite the shaft 408. The cap 440 is adapted to be impacted by a conventional hammer, not shown, used by the caretaker to impart force to the implant 1 via the instrument 402. More specifically, when the caretaker strikes the cap 440 with the hammer, the force of the strike is transmitted through the handle 404 to the shaft 408 to the impact head 406 and, ultimately, to the implant 1. The cap 440 is preferably made of durable metal so that the cap 440 is best able to receive and transmit the force imparted by the hammer strike.

Figure 26:
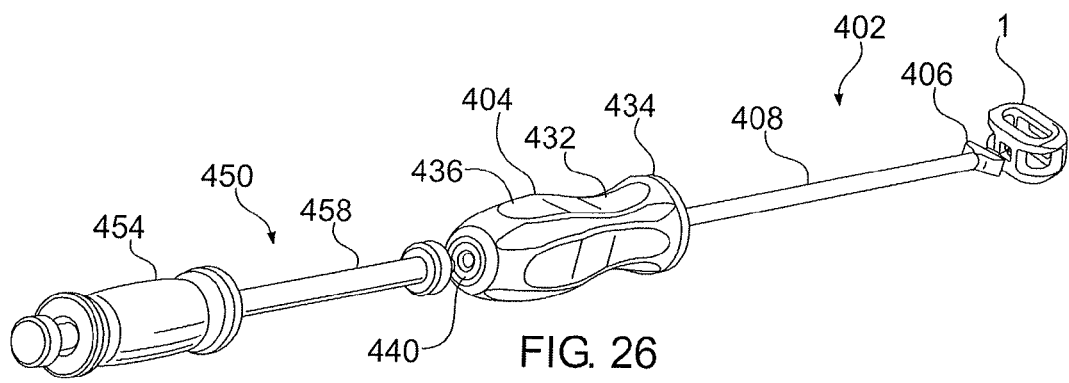
FIG. 26 shows a slap impacting hammer as used in connection with an instrument adapted to engage with and manipulate the implant according to another embodiment of the present invention.
Figure 27:
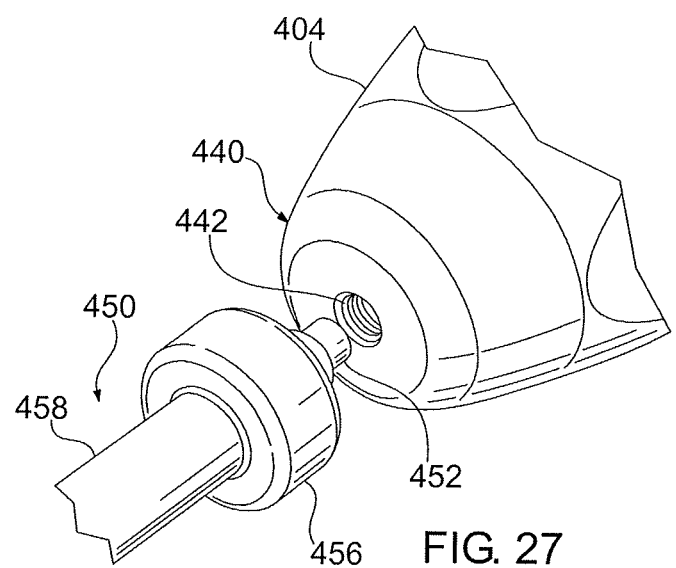
FIG. 27 illustrates the connection between the slap impacting hammer and the handle of the instrument shown in FIG. 26.

FIG. 26 shows a slap impacting hammer 450 as used in connection with the instrument 402 adapted to engage with and manipulate the implant 1 according to another embodiment of the present invention. The connection between the slap impacting hammer 450 and the handle 404 of the instrument 402 is highlighted in FIG. 27. As illustrated, the cap 440 has a threaded hole 442 which receives a corresponding threaded tip 452 of the head 456 of the slap impacting hammer 450. Other structural connections between the impacting hammer 450 and the handle 404 of the instrument 402 are both possible and within the knowledge of an artisan.

The slap impacting hammer 450 has a handle 454 which the caretaker can drive along the rod 458 into contact with the head 456. When the handle 454 "slaps" or contacts the head 456, force is imparted by the handle 454 to the head 456 and, in turn, to the handle 404 of the instrument 402 and, ultimately, to the implant 1. Thus, the slap impacting hammer 450 simply provides another way for the caretaker to impart force to the implant 1 using the instrument 402. The slap impacting hammer 450 also allows the caretaker to impart both insertion and removal forces to the implant 1 using the instrument 402.

Figure 28:
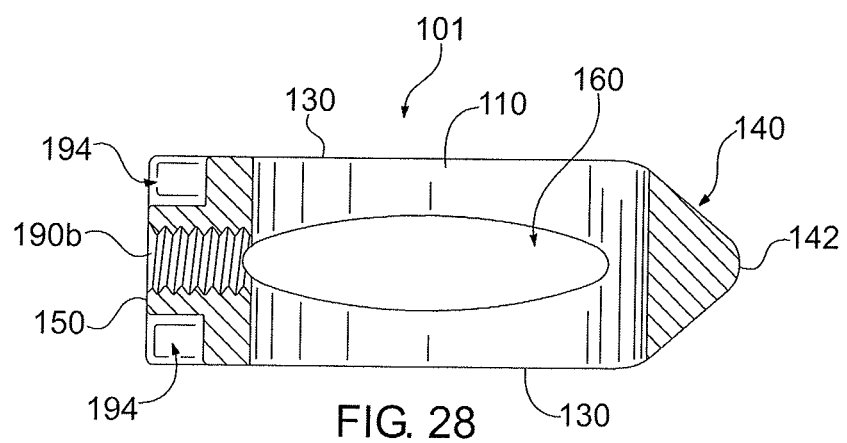
FIG. 28 shows a top view of an alternative embodiment of the interbody spinal implant shown in FIGS. 9 and 10, highlighting a threaded instrument connection.

Like the connection between the threaded hole 442 of the cap 440 and the threaded tip 452 of the head 456 of the slap impacting hammer 450, the connection between the instrument 402 and the implant 1, 101, 101a, 101b, and 201 can also be threaded. Such a threaded instrument-implant connection can be illustrated using the embodiment of the implant of FIGS. 9 and 10. Specifically, FIG. 28 shows a top view of an alternative embodiment of the interbody spinal implant 101 shown in FIGS. 9 and 10. All of the features of the implant 101 shown in FIG. 28 are substantially the same as the corresponding features shown in FIGS. 9 and 10 except that the opening 190 has been replaced by a threaded opening 190b.

FIG. 28 also shows example dimensions for various features of the implant 101. The structural columns that form the posterior 150 of the implant 101 are about 5.5 mm thick. The threaded opening 190b extends completely through the structural columns to the vertical aperture 160. The implant holding features 194, disposed on opposite sides of the threaded opening 190*b*, each have a length of about 3 mm (leaving a distance of about 2.5 mm from the closed ends of the implant holding features 194 to the ends of the structural columns). The width of the implant holding features 194 is also about 2.5 mm. The length of the anterior 140, which terminates in the nose 142, is about 4.8 mm. Two radii, each of about 3 mm, are provided at the nose 142 and at the transition between the lateral sides 130 and the anterior 140.

Figure 29:
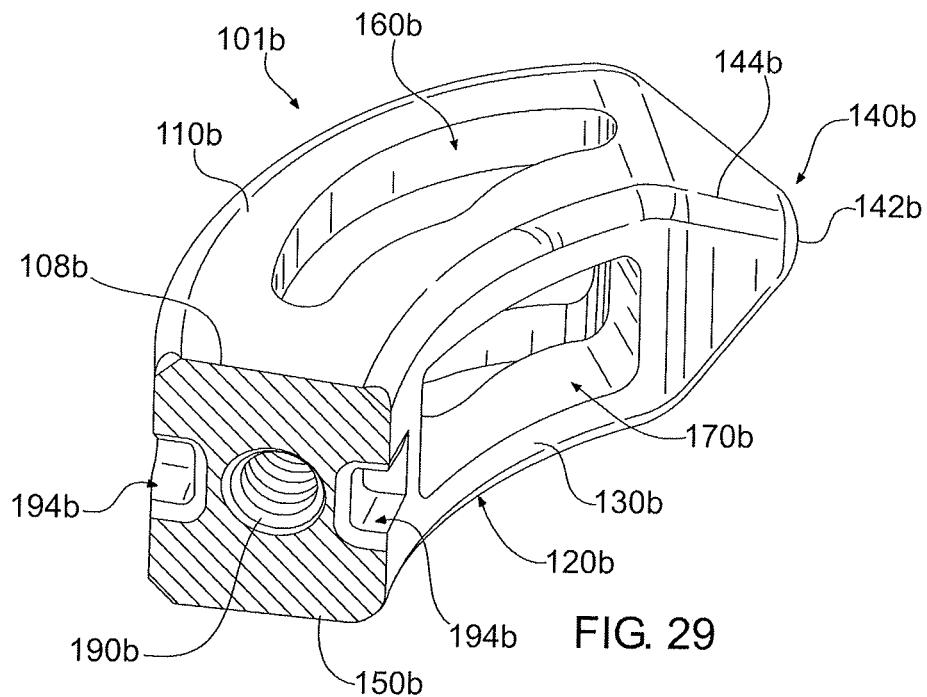
FIG. 29 shows a perspective view of an alternative embodiment of the interbody spinal implant shown in FIGS. 13-15, highlighting a threaded instrument connection.

A threaded instrument-implant connection can also be illustrated using the embodiment of the implant of FIGS. 13-15. Specifically, FIG. 29 shows a perspective view of an alternative embodiment of the interbody spinal implant 101*a* shown in FIGS. 13-15, namely the interbody spinal implant 101*b*, highlighting a threaded instrument connection 190*b*. All features shown in FIG. 28 that correspond with the features shown in FIGS. 13-15 are labeled with the letter "b" rather than the letter "a." The radiused features of the implant 101*b* that taper toward the nose 142*b* are assigned reference label 144*b*. In the embodiment illustrated in FIG. 28, the posterior 150*b* provides a large impact face for engagement with an embodiment of the instrument 402.

Figure 30:
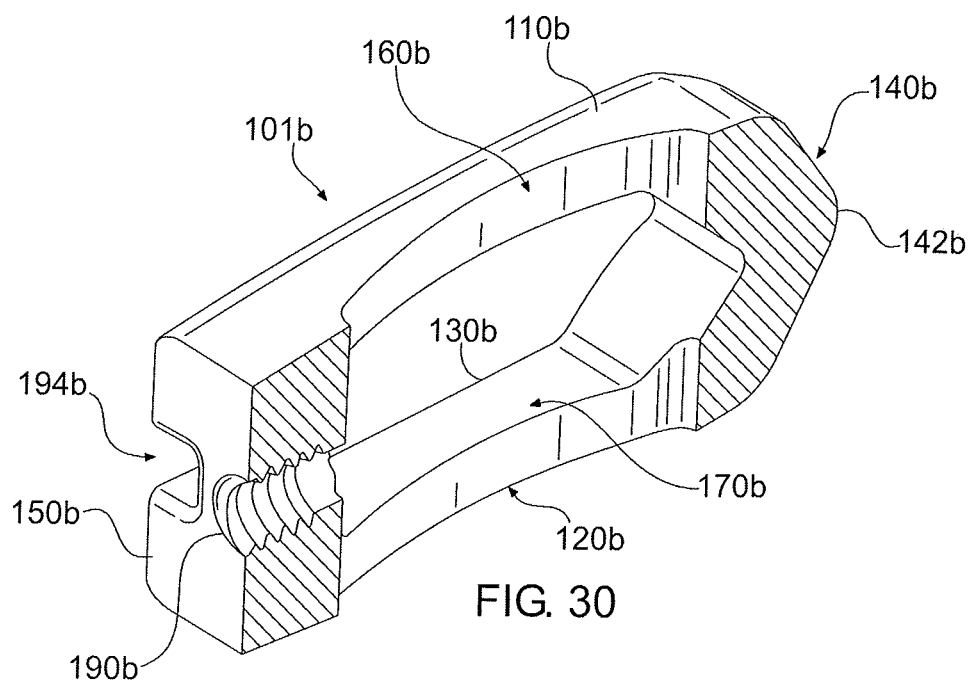
FIG. 30 is a perspective view, in partial cross section, showing example dimensions for various features of the implant shown in FIG. 29.

FIG. 30 is a perspective view, in partial cross section, showing example dimensions for various features of the implant 101*b*. The distance from the lateral sides 130*b* to the center of the threaded opening 190*b* is about 3.7 mm. The threaded opening 190*b* is centered in the posterior 150*b* and extends completely (about 3.5 mm) through the structural columns to the vertical aperture 160 (although, as shown, the threads may extend along only part of, rather than along the entire, length of the threaded opening 190*b*). The distance from the edges of the implant holding features 194 nearest the threaded opening 190*b* to the center of the threaded opening 190*b* is about 1.9 mm. The length of the anterior 140*b*, which terminates in the nose 142*b*, is about 4.8 mm. A radius of about 3 mm is provided at the transition between the top surface 110*b* and the anterior 140*b*. A radius of about 1 mm is provided at the transition between the top surface 110 and the lateral sides 130. The height of the lateral sides 130*b* from the bottom surface 120*b* to the transverse apertures 170*b* is about 1.7 mm.

Figure 31:
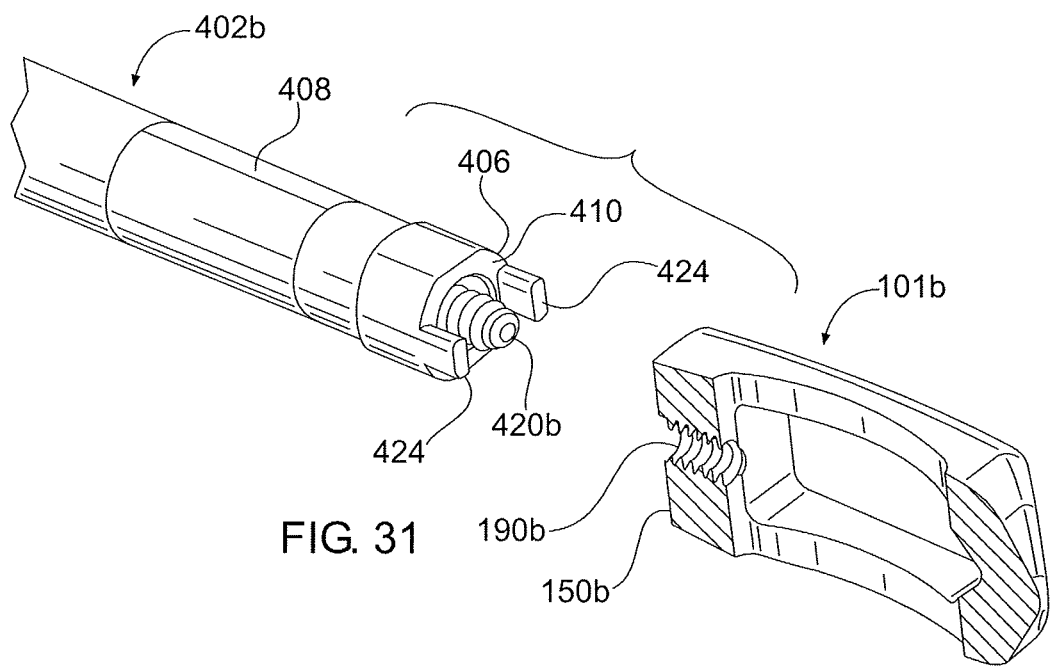
FIG. 31 illustrates an alternative embodiment of the instrument used to engage the implants, according to the present invention, each having both a threaded opening and implant holding features.

FIG. 31 illustrates an alternative embodiment of the instrument 402*b* used to engage the implants 101, 101*b*, shown in FIGS. 28-30, each having both a threaded opening 190*b* and implant holding features 194, 194*b*. FIG. 31 specifically shows the instrument 402*b* in combination with the implant 101*b* of FIGS. 29 and 30. The instrument 402*b* works just as well in combination with the implant 101 of FIG. 28, and with other implants (not shown) having a threaded opening 190*b* and implant holding features 194, 194*b*.

Like the instrument 402 shown in FIG. 23, the instrument 402*b* shown in FIG. 31 has a shaft 408 and an impact head 406. And the implant head 406 has an impact face 410 which engages the posterior 150*b* of the implant 101*b* when the instrument 402*b* is connected to the implant 101*b*. Rather than the unthreaded projection 420 of the instrument 402 shown in FIG. 23, however, the instrument 402*b* shown in FIG. 31 has a threaded projection 420*b*. The threaded projection 420*b* engages the threaded opening 190*b* of the implant 101*b* when the instrument 402*b* is connected to the implant 101*b*. Also unlike the instrument 402 shown in FIG. 23, the instrument 402*b* shown in FIG. 31 has at least one flange 424 (two flanges 424 are shown). The flanges 424 are sized and shaped to correspond with the implant holding features 194, 194*b* of the implant 101*b*. Thus, the flanges 424 are adapted to engage the implant holding features 194, 194*b* of the implant 101*b* when the instrument 402*b* is connected to the implant 101*b*. The flange or flanges 424 allow for off-axis adjustments to the positioning of the implant 101*b*.

Figure 32:
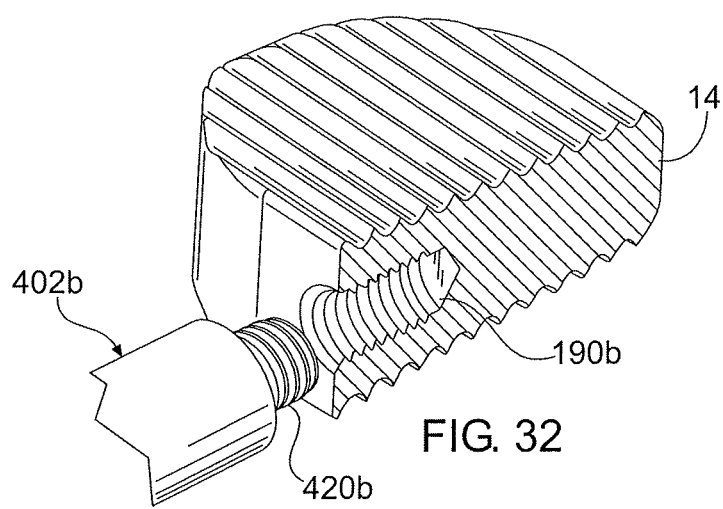
FIG. 32 illustrates the combination of (a) an embodiment of the instrument having a threaded projection with (b) an embodiment of the rasp having a threaded opening.

The implant holder 2 and any of the instruments 402, 402*b* discussed above can be used in combination with any of the implants 1, 101, 101*a*, 101*b*, and 201 discussed above (with appropriate modification, if necessary, of the opening 90, 190, 190*b*, and 290). The implant holder 2 and any of the instruments 402, 402*b* discussed above can also be used in combination with the distractor 12 (FIG. 7) and the rasp 14 (FIG. 8) discussed above (with appropriate modification, if necessary, of the instrument-receiving openings of the distractor 12 and the rasp 14). FIG. 32 illustrates the combination of (a) an embodiment of the instrument 402*b* having a threaded projection 420*b* (but without flanges 424), with (b) an embodiment of the rasp 14 having a threaded opening 190*b*. The slap impacting hammer 450 (discussed above) can be used in combination with the implant holder 2 and with any of the instruments 402, 402*b* to engage and manipulate the distractor 12 and the rasp 14.

Preferred embodiments of the present surgical method minimize endplate bone removal on the whole, while still allowing for some removal along the vertebral endplate far lateral edges where the subchondral bone is thickest. Still further, certain embodiments of the present interbody spinal implant 1, 101, 101*a*, 101*b*, and 201 include smooth, rounded, and highly radiused posterior portions and lateral sides which may minimize extraneous bone removal for endplate preparation and reduce localized stress concentrations. Thus, interbody surgical implants 1, 101, 101*a*, 101*b*, and 201 and methods of using them, as now taught, are particularly useful in preserving the natural arch of the vertebral endplate and minimizing the chance of implant subsidence.

Because the endplates are spared during the process of inserting the spinal implant 1, 101, 101*a*, 101*b*, and 201, hoop stress of the inferior and superior endplates is maintained. Spared endplates allow the transfer of axial stress to the apophasis. Endplate flexion allows the bone graft placed in the interior of the spinal implant 1, 101, 101*a*, 101*b*, and 201 to accept and share stress transmitted from the endplates. In addition, spared endplates minimize the concern that BMP might erode the cancellous bone.

Interbody spinal implants 1, 101, 101*a*, 101*b*, and 201 of the present invention are durable and can be impacted between the endplates with standard instrumentation. Therefore, certain embodiments of the present invention may be used as the final distractor during implantation. In this manner, the disc space may be under-distracted (e.g., distracted to some height less than the height of the interbody spinal implant 1, 101, 101*a*, 101*b*, and 201) to facilitate press-fit implantation. Further, certain embodiments of the current invention having a smooth and rounded posterior portion (and lateral sides) may facilitate easier insertion into the disc space. Still further, those embodiments having a surface roughened topography 80, 180, 180*a*, and 280, as now taught, may lessen the risk of excessive bone removal during distraction as compared to implants having teeth, ridges, or threads currently known in the art even in view of a press-fit surgical distraction method. Nonetheless, once implanted, the interbody surgical implants 1, 101, 101*a*, 101*b*, and 201, as now taught, may provide secure seating and prove difficult to remove. Thus, certain embodiments of the present interbody spinal implant 1, 101, 101*a*, 101*b*, and 201 may maintain a position between the vertebral endplates due, at least in part, to resultant annular tension attributable to press-fit surgical implantation and, post-operatively, improved osteointegration at the top surface 10, 110, 110a, and 210, the bottom surface 20, 120, 120a, and 220, or both top and bottom surfaces.

As previously mentioned, surgical implants and methods, as now taught, tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implants 1, 101, 101a, 101b, and 201, according to certain embodiments of the present invention, are particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implants 1, 101, 101a, 101b, and 201 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implants 1, 101, 101a, 101b, and 201, as now taught, may be used as the final distractor and thus maintain the relative position of the vertebrae without the need for secondary instrumentation.

Certain embodiments collectively comprise a family of implants, each having a common design philosophy. These implants and the associated surgical technique have been designed to address the ten, separate challenges associated with the current generation of traditional anterior spinal fusion devices listed above in the Background section of this document. Each of these challenges is addressed in turn and in the order listed above.

1. End-Plate Preparation

Embodiments of the present invention allow end-plate preparation with custom-designed rasps 14. These rasps 14 have a geometry matched with the geometry of the implant. The rasps 14 conveniently remove cartilage from the end-plates and remove minimal bone, only in the postero-lateral regions of the vertebral end-plates. It has been reported in the literature that the end-plate is the strongest in postero-lateral regions.

2. Implant Difficulty

After desired annulotomy and discectomy, embodiments of the present invention first adequately distract the disc space by inserting (through impaction) and removing sequentially larger sizes of very smooth distractors, which have size matched with the size of the available implants 1, 101, 101a, 101b, and 201. Once adequate distraction is achieved, the surgeon prepares the end-plate with a size-specific rasp 14. There is no secondary instrumentation required to keep the disc space distracted while the implant 1, 101, 101a, 101b, and 201 is inserted, as the implant 1, 101, 101a, 101b, and 201 has sufficient mechanical strength that it is impacted into the disc space. In fact, the height of the implant 1, 101, 101a, 101b, and 201 is about 1 mm greater than the height of the rasp 14 used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101a, 101b, and 201 is designed such that all the impact loads are applied only to the titanium part of the construct. Thus, the implant 1, 101, 101a, 101b, and 201 has adequate strength to allow impact. The sides of the implant 1, 101, 101a, 101b, and 201 have smooth surfaces to allow for easy implantation and, specifically, to prevent "binding" of the implant 1, 101, 101a, 101b, and 201 to soft tissues during implantation.

3. Materials of Construction

The present invention encompasses a number of different implants 1, 101, 101a, 101b, and 201, including a one-piece, titanium-only implant and a composite implant formed of top and bottom plates 162 (components) made out of titanium. The surfaces exposed to the vertebral body are dual acid etched to allow for bony in-growth over time, and to provide resistance against expulsion. The top and bottom titanium plates 162 are assembled together with the implant body 152 that is injection molded with PEEK. The net result is a composite implant 101a that has engineered stiffness for its clinical application. The axial load is borne by the PEEK component of the construct.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101a, 101b, and 201 designed according to certain embodiments of the present invention allows the vertebral end-plate to deflect and allows healing of the bone graft into fusion.

4. Implant Expulsion

Certain faces of the implant 1, 101, 101a, 101b, and 201 according to certain embodiments of the present invention have sharp edges 8, 180. These edges 8, 180 tend to dig "into" the end-plates slightly and help to resist expulsion. The top and bottom surfaces of the implant are made out of titanium and are dual acid etched. The dual acid etching process creates a highly roughened texture on these surfaces, which generates tremendous resistance to expulsion. The width of these dual acid etched surfaces is very broad and creates a large area of contact with the vertebral end-plates, further increasing the resistance to expulsion.

5. Implant Subsidence

The implant 1, 101, 101a, 101b, and 201 according to certain embodiments of the present invention has a large foot-print, and offers several sizes. Because there is no secondary instrument required to maintain distraction during implantation, all the medial-lateral (ML) exposure is available as implantable ML width of the implant. This feature allows the implant to contact the vertebral end-plates at the peripheral apophyseal rim, where the end-plates are the strongest and least likely to subside.

Further, there are no teeth on the top and bottom surfaces (teeth can create stress risers in the end-plate, encouraging subsidence). Except for certain faces, all the implant surfaces have heavily rounded edges, creating a low stress contact with the end-plates. The wide rim of the top and bottom surfaces, in contact with the end-plates, creates a low-stress contact due to the large surface area. Finally, the implant construct has an engineered stiffness to minimize the stiffness mismatch with the vertebral body which it contacts.

6. Insufficient Room for Bone Graft

As mentioned, the implant 1, 101, 101*a*, 101*b*, and 201 according to certain embodiments of the present invention has a large foot-print. In addition, titanium provides high strength for a small volume. In combination, the large footprint along with the engineered use of titanium allows for a large volume of bone graft to be placed inside the implant.

7. Stress Shielding

As stated above, it is believed that an intact vertebral end-plate deflects like a diaphragm under axial compressive loads generated due to physiologic activities. If a spinal fusion implant is inserted in the prepared disc space via a procedure which does not destroy the end-plate, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101*a*, 101*b*, and 201 according to certain embodiments of the present invention allows the vertebral end-plate to deflect and facilitates healing of the bone graft into fusion.

8. Lack of Implant Incorporation with Vertebral Bone

The top and bottom surfaces of the implant 1, 101, 101*a*, 101*b*, and 201 according to certain embodiments of the present invention are made of titanium and are dual acid etched. The dual acid etched surface treatment of titanium allows in-growth of bone to the surfaces. Hence, the implant 1, 101, 101*a*, 101*b*, and 201 is designed to incorporate with the vertebral bone over time. It may be that the in-growth happens sooner than fusion. If so, there may be an opportunity for the patients treated with the implant 1, 101, 101*a*, 101*b*, and 201 of the present invention to return to normal activity levels sooner than currently recommended by standards of care.

9. Limitations on Radiographic Visualization

Even the titanium-only embodiment of the present invention has been designed with large windows to allow for radiographic evaluation of fusion, both through AP and lateral X-rays. The composite implant 101*a* minimizes the volume of titanium, and localizes it to the top and bottom surfaces. The rest of the implant 101*a* is made of PEEK which is radiolucent and allows for free radiographic visualization.

10. Cost of Manufacture and Inventory

The cost to manufacture a single implant 1, 101, 101*a*, 101*b*, and 201 according to the present invention is comparable to the cost to manufacture commercially available products. But a typical implant set for a conventional device can have three foot-prints and ten heights for each foot-print. Therefore, to produce one set, the manufacturer has to make thirty different setups if the implants are machined. In contrast, for the composite embodiment according to certain embodiments of the present invention, the manufacturer will have to machine only three sets of metal plates, which is six setups. The PEEK can be injection molded between the metal plates separated by the distance dictated by the height of the implant 101*a*. Once the injection molds are made, the subsequent cost of injection molding is considerably less as compared to machining. This feature of the present invention can lead to considerable cost savings.

In addition, a significant expense associated with a dual acid etched part is the rate of rejects due to acid leaching out to surfaces which do not need to be etched. In the case of the composite implant 101*a* according to certain embodiments of the present invention, the criteria for acceptance of such a part will be lower because the majority of the surfaces are covered with PEEK via injection molding after the dual acid etching process step. This feature can yield significant manufacturing-related cost savings.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment. It is also expressly intended that the steps of the methods of using the various devices disclosed above are not restricted to any particular order.

What is claimed:

1. An apparatus for distracting a disc space having an annulus, the apparatus comprising a spinal implant having:
    a pre-determined size sufficient to balance frictional fit in the disc space and elongation of the annulus;
    a top surface, a bottom surface, opposing lateral sides, and opposing anterior and posterior portions defining a substantially hollow center and a single vertical aperture defining a perimeter, the single vertical aperture (a) extending from the top surface to the bottom surface, (b) having a size and shape predetermined to maximize the surface area of the top surface and the bottom surface available proximate the anterior and posterior portions while maximizing both radiographic visualization and access to the substantially hollow center, and (c) defining a transverse rim of varying thickness;
    a roughened surface topography, without teeth, on at least a portion of the top surface, the bottom surface, or both the top and bottom surfaces surrounding the entire perimeter of the single vertical aperture and adapted to grip bone and inhibit migration of the implant;
    at least one sharp edge between the top and bottom surfaces and the anterior portion or the posterior portion to resist pullout;
    generally rounded and blunt intersections defined along the entire lengths between the top and bottom surfaces and the lateral sides, and either the top and bottom surfaces and the posterior portion or the top and bottom surfaces and the anterior portion, which do not comprise the at least one sharp edge; and
    at least one of the opposing anterior and posterior portions presenting a substantially flat impact face including an opening with an instrument retention feature.

2. The apparatus of claim 1, wherein the instrument retention feature is threaded.

3. The apparatus of claim 1, wherein the instrument retention feature is at least one notch.

4. The apparatus of claim 1, wherein the opening in the impact face has a radiused insertion feature.

5. The apparatus of claim 1, wherein the opening is centrally positioned on the impact face.

6. The apparatus of claim 1, wherein the spinal implant has a plurality of structural columns between the top and bottom surfaces.

7. The apparatus of claim 1 further comprising an instrument able to engage and manipulate the spinal implant, the instrument having a handle, a rigid shaft, and an impact head.

8. The apparatus of claim 7, wherein the handle of the instrument has curved indentations, a rim, a bulbous portion, and substantially smooth surfaces.

9. The apparatus of claim 7, wherein the handle of the instrument has a cap on its end opposite the shaft, the cap adapted to be impacted by a hammer.

10. The apparatus of claim 7, wherein the impact head of the instrument has a substantially flat impact face that contacts the substantially flat impact face of the spinal implant when the instrument engages the spinal implant.

11. The apparatus of claim 10, wherein the impact head of the instrument has a projection that is inserted into the opening of the impact face of the spinal implant when the instrument engages the spinal implant.

12. The apparatus of claim 11, wherein the projection extends from the impact face of the impact head of the instrument perpendicularly away from the impact face and is disposed centrally on the impact face.

13. The apparatus of claim 12, wherein the projection is axially aligned with the shaft.

14. The apparatus of claim 11, wherein the opening in the impact face of the spinal implant has a radiused insertion feature and the projection of the impact head of the instrument has a plurality of chamfers that correspond to the radiused insertion feature of the spinal implant to facilitate insertion of the projection into the opening.

15. The apparatus of claim 11, wherein the projection has one or more nubs that engage the instrument retention feature upon insertion of the projection into the opening.

16. The apparatus of claim 7 wherein the spinal implant has an implant holding feature disposed on the impact face and the instrument has at least one flange sized and shaped to correspond with the implant holding feature, the flange engaging the implant holding feature when the instrument engages the spinal implant.

17. The apparatus of claim 7 further comprising a slap impacting hammer for connection to the handle of the instrument and imparting force to the handle.

18. The apparatus of claim 7 further comprising a size-specific rasp adapted to clear the disc space of all soft tissue and cartilage, the instrument able to engage and manipulate the rasp.

19. The apparatus of claim 7 further comprising a plurality of distractors of progressively increasing heights adapted to distract the disc space before use of the spinal implant, the instrument able to engage and manipulate the distractors.

20. The apparatus of claim 1, wherein the opening comprises a square formed of four equal faces and the instrument retention feature comprises at least one notch.

21. An apparatus for distracting a disc space having an annulus, the apparatus comprising:
 a spinal implant having:
  (a) a pre-determined size sufficient to balance frictional fit in the disc space and elongation of the annulus,
  (b) a top surface, a bottom surface, opposing lateral sides, and opposing anterior and posterior portions defining a substantially hollow center and a single vertical aperture defining a perimeter, the single vertical aperture (i) extending from the top surface to the bottom surface, (ii) having a size and shape predetermined to maximize the surface area of the top surface and the bottom surface available proximate the anterior and posterior portions while maximizing both radiographic visualization and access to the substantially hollow center, and (iii) defining a transverse rim of varying width,
  (c) a roughened surface topography, without teeth, on at least a portion of the top surface, the bottom surface, or both the top and bottom surfaces surrounding the entire perimeter of the single vertical aperture and adapted to grip bone and inhibit migration of the implant,
  (d) at least one sharp edge between the top and bottom surfaces and the anterior portion or the posterior portion to resist pullout,
  (e) generally rounded and blunt intersections defined along the entire lengths between the top and bottom surfaces and the lateral sides, and either the top and bottom surfaces and the posterior portion or the top and bottom surfaces and the anterior portion, which do not comprise the at least one sharp edge; and
  (f) at least one of the opposing anterior and posterior portions presenting a substantially flat impact face including an opening with an instrument retention feature;
 an instrument able to engage and manipulate the spinal implant, the instrument having:
  (a) a handle,
  (b) a rigid shaft, and
  (c) an impact head with a substantially flat impact face and a projection, the impact face contacting the impact face of the spinal implant and the projection being inserted into the opening of the impact face of the spinal implant when the instrument engages the spinal implant;
 a size-specific rasp adapted to clear the disc space of all soft tissue and cartilage, the instrument able to engage and manipulate the rasp; and
 a plurality of distractors of progressively increasing heights adapted to distract the disc space before use of the spinal implant, the instrument able to engage and manipulate the distractors.

* * * * *